(12) United States Patent (10) Patent No.: US 9,198,608 B2
Hafezi et al. (45) Date of Patent: Dec. 1, 2015

(54) COMMUNICATION SYSTEM INCORPORATED IN A CONTAINER

(75) Inventors: Hooman Hafezi, Redwood City, CA (US); David O'Reilly, Palo Alto, CA (US); Patricia Johnson, Palo Alto, CA (US); Zahedeh Hatamkhany, San Mateo, CA (US); Timothy Robertson, Belmont, CA (US); Mark Zdeblick, Portola Valley, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 501 days.

(21) Appl. No.: 13/304,274

(22) Filed: Nov. 23, 2011

(65) Prior Publication Data

US 2012/0299723 A1 Nov. 29, 2012

(51) Int. Cl.
| | |
|---|---|
| *G08B 13/14* | (2006.01) |
| *A61B 5/145* | (2006.01) |
| *A61B 5/07* | (2006.01) |
| *A61J 3/00* | (2006.01) |
| *H01Q 1/27* | (2006.01) |
| *A61B 5/01* | (2006.01) |
| *A61B 5/03* | (2006.01) |
| *A61B 5/1473* | (2006.01) |
| *A61B 5/00* | (2006.01) |

(Continued)

(52) U.S. Cl.
CPC .............. *A61B 5/14539* (2013.01); *A61B 5/073* (2013.01); *A61J 3/007* (2013.01); *H01Q 1/273* (2013.01); *A61B 5/01* (2013.01); *A61B 5/036* (2013.01); *A61B 5/1473* (2013.01); *A61B 5/4839* (2013.01); *A61B 2562/0214* (2013.01); *H04B 1/3888* (2013.01); *H04B 2001/3894* (2013.01)

(58) Field of Classification Search
CPC .. A61B 5/0026; A61B 5/0028; A61B 5/0031; A61B 5/6861; A61B 5/14539; A61B 5/073; A61B 2562/162; A61J 3/007; A61J 2205/60; H01Q 1/273
See application file for complete search history.

(56) References Cited

U.S. PATENT DOCUMENTS

| | | | |
|---|---|---|---|
| 3,589,943 | A | 6/1971 | Grubb et al. |
| 3,607,788 | A | 9/1971 | Adolph |

(Continued)

FOREIGN PATENT DOCUMENTS

| | | |
|---|---|---|
| CN | 1588649 | 3/2005 |
| CN | 1991868 | 7/2007 |

(Continued)

OTHER PUBLICATIONS

AADE, "AADE 37th Annual Meeting San Antonio Aug. 4-7, 2010" American Association of Diabetes Educators (2010); http://www.diabeteseducator.org/annualmeeting/2010/index.html; 2 pages.

(Continued)

*Primary Examiner* — Firmin Backer
*Assistant Examiner* — Brian Wilson
(74) *Attorney, Agent, or Firm* — K&L Gates LLP

(57) ABSTRACT

The system of the present invention includes a container and an electronic component with a partial power source in the form of dissimilar materials. The container includes a liquid. Upon contact with the liquid, a voltage potential is created and the power source is completed, which activates the system. The electronic component controls the conductance between the dissimilar materials to produce a unique current signature.

15 Claims, 8 Drawing Sheets

(51) Int. Cl.
*H04B 1/3888* (2015.01)
*H04B 1/38* (2015.01)

(56) References Cited

U.S. PATENT DOCUMENTS

| | | | |
|---|---|---|---|
| 3,628,669 A | 12/1971 | McKinnis et al. |
| 3,642,008 A | 2/1972 | Bolduc |
| 3,679,480 A | 7/1972 | Brown et al. |
| 3,682,160 A | 8/1972 | Murata |
| 3,719,183 A | 3/1973 | Schwartz |
| 3,727,616 A | 4/1973 | Lenzkes |
| 3,799,802 A | 3/1974 | Schneble, Jr. et al. |
| 3,828,766 A | 8/1974 | Krasnow |
| 3,837,339 A | 9/1974 | Aisenberg et al. |
| 3,893,111 A | 7/1975 | Cotter |
| 3,944,064 A | 3/1976 | Bashaw et al. |
| 3,967,202 A | 6/1976 | Batz |
| 3,989,050 A | 11/1976 | Buchalter |
| 4,017,856 A | 4/1977 | Wiegand |
| 4,055,178 A | 10/1977 | Harrigan |
| 4,062,750 A | 12/1977 | Butler |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,106,348 A | 8/1978 | Auphan |
| 4,129,125 A | 12/1978 | Lester |
| 4,141,349 A | 2/1979 | Ory et al. |
| 4,166,453 A | 9/1979 | McClelland |
| 4,239,046 A | 12/1980 | Ong |
| 4,251,795 A | 2/1981 | Shibasaki et al. |
| 4,269,189 A | 5/1981 | Abraham |
| 4,281,664 A | 8/1981 | Duggan |
| 4,331,654 A | 5/1982 | Morris |
| 4,345,588 A | 8/1982 | Widder et al. |
| 4,418,697 A | 12/1983 | Tama |
| 4,425,117 A | 1/1984 | Hugemann |
| 4,439,196 A | 3/1984 | Higuchi |
| 4,494,950 A | 1/1985 | Fischell |
| 4,559,950 A | 12/1985 | Vaughan |
| 4,564,363 A | 1/1986 | Bagnall et al. |
| 4,578,061 A | 3/1986 | Lemelson |
| 4,635,641 A | 1/1987 | Hoffman |
| 4,654,165 A | 3/1987 | Eisenberg |
| 4,663,250 A | 5/1987 | Ong et al. |
| 4,669,479 A | 6/1987 | Dunseath |
| 4,681,111 A | 7/1987 | Silvian |
| 4,687,660 A | 8/1987 | Baker et al. |
| 4,725,997 A | 2/1988 | Urquhart et al. |
| 4,749,575 A | 6/1988 | Rotman et al. |
| 4,763,659 A | 8/1988 | Dunseath |
| 4,767,627 A | 8/1988 | Caldwell et al. |
| 4,784,162 A | 11/1988 | Ricks |
| 4,793,825 A | 12/1988 | Benjamin et al. |
| 4,809,705 A | 3/1989 | Ascher |
| 4,844,076 A | 7/1989 | Lesho |
| 4,871,974 A | 10/1989 | Davis et al. |
| 4,876,093 A | 10/1989 | Theeuwes et al. |
| 4,896,261 A | 1/1990 | Nolan |
| 4,975,230 A | 12/1990 | Pinkhasov |
| 4,987,897 A | 1/1991 | Funke |
| 5,000,957 A | 3/1991 | Eckenhoff et al. |
| 5,016,634 A | 5/1991 | Vock et al. |
| 5,079,006 A | 1/1992 | Urquhart |
| 5,167,626 A | 12/1992 | Casper |
| 5,176,626 A | 1/1993 | Soehendra |
| 5,179,578 A | 1/1993 | Ishizu |
| 5,245,332 A | 9/1993 | Katzenstein et al. |
| 5,261,402 A | 11/1993 | DiSabito |
| 5,263,481 A | 11/1993 | Axelgaard et al. |
| 5,279,607 A | 1/1994 | Schentag et al. |
| 5,281,287 A | 1/1994 | Lloyd |
| 5,283,136 A | 2/1994 | Peled et al. |
| 5,305,745 A | 4/1994 | Zacouto |
| 5,318,557 A | 6/1994 | Gross |
| 5,394,882 A | 3/1995 | Mawhinney |
| 5,395,366 A | 3/1995 | D'Andrea et al. |
| 5,436,091 A | 7/1995 | Shackle et al. |
| 5,443,461 A | 8/1995 | Atkinson et al. |
| 5,443,843 A | 8/1995 | Curatolo et al. |
| 5,458,141 A | 10/1995 | Neil et al. |
| 5,485,841 A | 1/1996 | Watkin et al. |
| 5,511,548 A | 4/1996 | Riazzi et al. |
| 5,567,210 A | 10/1996 | Bates et al. |
| 5,596,302 A | 1/1997 | Mastrocola et al. |
| D377,983 S | 2/1997 | Sabri et al. |
| 5,600,548 A | 2/1997 | Nguyen et al. |
| 5,634,466 A | 6/1997 | Gruner |
| 5,634,468 A | 6/1997 | Platt |
| 5,645,063 A | 7/1997 | Straka et al. |
| 5,705,189 A | 1/1998 | Lehmann et al. |
| 5,720,771 A | 2/1998 | Snell |
| 5,738,708 A | 4/1998 | Peachey et al. |
| 5,740,811 A | 4/1998 | Hedberg |
| 5,757,326 A | 5/1998 | Koyama et al. |
| 5,792,048 A | 8/1998 | Schaefer |
| 5,802,467 A | 9/1998 | Salazar |
| 5,833,716 A | 11/1998 | Bar-Or |
| 5,845,265 A | 12/1998 | Woolston |
| 5,862,803 A | 1/1999 | Besson |
| 5,862,808 A | 1/1999 | Albarello |
| 5,868,136 A | 2/1999 | Fox |
| 5,921,925 A | 7/1999 | Cartmell et al. |
| 5,925,030 A | 7/1999 | Gross et al. |
| 5,925,066 A | 7/1999 | Kroll et al. |
| 5,957,854 A | 9/1999 | Besson et al. |
| 5,963,132 A | 10/1999 | Yoakum et al. |
| 5,974,124 A | 10/1999 | Schlueter, Jr. et al. |
| 5,981,166 A | 11/1999 | Mandecki |
| 5,999,846 A | 12/1999 | Pardey et al. |
| 6,009,350 A | 12/1999 | Renken |
| 6,023,631 A | 2/2000 | Cartmell et al. |
| 6,038,464 A | 3/2000 | Axelgaard et al. |
| 6,042,710 A | 3/2000 | Dubrow |
| 6,047,203 A | 4/2000 | Sackner |
| 6,076,016 A | 6/2000 | Feierbach et al. |
| 6,081,734 A | 6/2000 | Batz |
| 6,083,248 A | 7/2000 | Thompson |
| 6,090,489 A | 7/2000 | Hayakawa et al. |
| 6,091,975 A | 7/2000 | Daddona et al. |
| 6,095,985 A | 8/2000 | Raymond et al. |
| 6,115,636 A | 9/2000 | Ryan |
| 6,117,077 A | 9/2000 | Del Mar et al. |
| 6,122,351 A | 9/2000 | Schlueter, Jr. et al. |
| 6,141,592 A | 10/2000 | Pauly |
| 6,149,940 A | 11/2000 | Maggi et al. |
| 6,200,265 B1 | 3/2001 | Walsh et al. |
| 6,204,764 B1 | 3/2001 | Maloney |
| 6,206,702 B1 | 3/2001 | Hayden et al. |
| 6,217,744 B1 | 4/2001 | Crosby |
| 6,231,593 B1 | 5/2001 | Meserol |
| 6,245,057 B1 | 6/2001 | Sieben et al. |
| 6,269,058 B1 | 7/2001 | Yamanoi et al. |
| 6,275,476 B1 | 8/2001 | Wood |
| 6,285,897 B1 | 9/2001 | Kilcoyne et al. |
| 6,287,252 B1 | 9/2001 | Lugo |
| 6,288,629 B1 | 9/2001 | Cofino et al. |
| 6,289,238 B1 | 9/2001 | Besson et al. |
| 6,315,719 B1 | 11/2001 | Rode et al. |
| 6,342,774 B1 | 1/2002 | Kreisinger et al. |
| 6,344,824 B1 | 2/2002 | Takasugi et al. |
| 6,358,202 B1 | 3/2002 | Arent |
| 6,364,834 B1 | 4/2002 | Reuss |
| 6,366,206 B1 | 4/2002 | Ishikawa et al. |
| 6,368,190 B1 | 4/2002 | Easter et al. |
| 6,371,927 B1 | 4/2002 | Brune |
| 6,374,670 B1 | 4/2002 | Spelman |
| 6,380,858 B1 | 4/2002 | Yarin et al. |
| 6,390,088 B1 | 5/2002 | Nohl et al. |
| 6,394,953 B1 | 5/2002 | Devlin et al. |
| 6,394,997 B1 | 5/2002 | Lemelson |
| 6,409,674 B1 | 6/2002 | Brockway et al. |
| 6,426,863 B1 | 7/2002 | Munshi |
| 6,432,292 B1 | 8/2002 | Pinto et al. |

(56) References Cited

U.S. PATENT DOCUMENTS

| | | | |
|---|---|---|---|
| 6,440,069 B1 | 8/2002 | Raymond et al. |
| 6,441,747 B1 | 8/2002 | Khair |
| 6,453,199 B1 | 9/2002 | Kobozev |
| 6,477,424 B1 | 11/2002 | Thompson et al. |
| 6,482,156 B2 | 11/2002 | Lliff |
| 6,494,829 B1 | 12/2002 | New et al. |
| 6,496,705 B1 | 12/2002 | Ng et al. |
| 6,505,077 B1 | 1/2003 | Kast et al. |
| 6,526,315 B1 | 2/2003 | Inagawa |
| 6,531,026 B1 | 3/2003 | Takeichi et al. |
| 6,540,699 B1 | 4/2003 | Smith |
| 6,544,174 B2 | 4/2003 | West |
| 6,564,079 B1 | 5/2003 | Cory |
| 6,572,636 B1 | 6/2003 | Hagen et al. |
| 6,574,425 B1 | 6/2003 | Weiss et al. |
| 6,577,893 B1 | 6/2003 | Besson et al. |
| 6,579,231 B1 | 6/2003 | Phipps |
| 6,595,929 B2 | 7/2003 | Stivoric |
| 6,599,284 B2 | 7/2003 | Faour et al. |
| 6,605,038 B1 | 8/2003 | Teller |
| 6,605,046 B1 | 8/2003 | Del Mar |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,635,279 B2 | 10/2003 | Kolter et al. |
| 6,643,541 B2 | 11/2003 | Mok et al. |
| 6,650,718 B1 | 11/2003 | Fujimura et al. |
| 6,654,638 B1 | 11/2003 | Sweeney |
| 6,663,846 B1 | 12/2003 | McCombs |
| 6,673,474 B2 | 1/2004 | Yamamoto |
| 6,680,923 B1 | 1/2004 | Leon |
| 6,683,493 B1 | 1/2004 | Fujimora et al. |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,759,968 B2 | 7/2004 | Zierolf |
| 6,773,429 B2 | 8/2004 | Sheppard et al. |
| 6,800,060 B2 | 10/2004 | Marshall |
| 6,801,137 B2 | 10/2004 | Eggers et al. |
| 6,804,558 B2 | 10/2004 | Haller et al. |
| 6,814,706 B2 | 11/2004 | Barton et al. |
| 6,822,554 B2 | 11/2004 | Vrijens et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |
| 6,879,810 B2 | 4/2005 | Bouet |
| 6,882,881 B1 | 4/2005 | Lesser et al. |
| 6,897,788 B2 | 5/2005 | Khair et al. |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,939,292 B2 | 9/2005 | Mizuno |
| 6,942,616 B2 | 9/2005 | Kerr |
| 6,951,536 B2 | 10/2005 | Yokoi |
| 6,957,107 B2 | 10/2005 | Rogers et al. |
| 6,959,929 B2 | 11/2005 | Pugnet et al. |
| 6,968,153 B1 | 11/2005 | Heinonen |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,023,940 B2 | 4/2006 | Nakamura et al. |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,050,419 B2 | 5/2006 | Azenkot et al. |
| 7,062,308 B1 | 6/2006 | Jackson |
| 7,076,437 B1 | 7/2006 | Levy |
| 7,081,693 B2 | 7/2006 | Hamel et al. |
| 7,118,531 B2 | 10/2006 | Krill |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |
| 7,161,484 B2 | 1/2007 | Tsoukalis |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,285,090 B2 | 10/2007 | Stivoric et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,295,877 B2 | 11/2007 | Govari |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,366,675 B1 | 4/2008 | Walker et al. |
| 7,368,190 B2 | 5/2008 | Heller et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |

(56) References Cited

U.S. PATENT DOCUMENTS

| | | | |
|---|---|---|---|
| 7,414,543 B2 | 8/2008 | Rye et al. | |
| 7,415,242 B1 | 8/2008 | Ngan | |
| 7,419,468 B2 | 9/2008 | Shimizu et al. | |
| 7,424,268 B2 | 9/2008 | Diener | |
| 7,424,319 B2 | 9/2008 | Muehlsteff | |
| 7,427,266 B2 | 9/2008 | Ayer et al. | |
| 7,471,665 B2 | 12/2008 | Perlman | |
| 7,499,674 B2 | 3/2009 | Salokannel | |
| 7,502,643 B2 | 3/2009 | Farringdon et al. | |
| 7,505,795 B1 | 3/2009 | Lim et al. | |
| 7,508,248 B2 | 3/2009 | Yoshida | |
| 7,510,121 B2 | 3/2009 | Koenck | |
| 7,512,448 B2 | 3/2009 | Malick | |
| 7,512,860 B2 | 3/2009 | Miyazaki et al. | |
| 7,515,043 B2 | 4/2009 | Welch | |
| 7,519,416 B2 | 4/2009 | Sula et al. | |
| 7,523,756 B2 | 4/2009 | Minai | |
| 7,525,426 B2 | 4/2009 | Edelstein | |
| 7,539,533 B2 | 5/2009 | Tran | |
| 7,542,878 B2 | 6/2009 | Nanikashvili | |
| 7,551,590 B2 | 6/2009 | Haller | |
| 7,554,452 B2 | 6/2009 | Cole | |
| 7,558,620 B2 | 7/2009 | Ishibashi | |
| 7,575,005 B2 | 8/2009 | Mumford | |
| 7,616,111 B2 | 11/2009 | Covannon | |
| 7,616,710 B2 | 11/2009 | Kim et al. | |
| 7,617,001 B2 | 11/2009 | Penner et al. | |
| 7,639,473 B2 | 12/2009 | Hsu et al. | |
| 7,640,802 B2 | 1/2010 | King et al. | |
| 7,647,112 B2 | 1/2010 | Tracey | |
| 7,647,185 B2 | 1/2010 | Tarassenko et al. | |
| 7,653,031 B2 | 1/2010 | Godfrey et al. | |
| 7,668,437 B1 | 2/2010 | Yamada et al. | |
| 7,672,703 B2 | 3/2010 | Yeo et al. | |
| 7,672,714 B2 | 3/2010 | Kuo | |
| 7,673,679 B2 | 3/2010 | Harrison et al. | |
| 7,678,043 B2 | 3/2010 | Gilad | |
| 7,689,437 B1 | 3/2010 | Teller et al. | |
| 7,697,994 B2 | 4/2010 | VanDanacker et al. | |
| 7,712,288 B2 | 5/2010 | Ramasubramanian et al. | |
| 7,720,036 B2 | 5/2010 | Sadri | |
| 7,729,776 B2 | 6/2010 | Von Arx et al. | |
| 7,733,224 B2 | 6/2010 | Tran | |
| 7,736,318 B2 | 6/2010 | Cosentino | |
| 7,756,587 B2 | 7/2010 | Penner et al. | |
| 7,779,614 B1 | 8/2010 | McGonagle et al. | |
| 7,796,043 B2 | 9/2010 | Euliano et al. | |
| 7,797,033 B2 | 9/2010 | D'Andrea et al. | |
| 7,806,852 B1 | 10/2010 | Jurson | |
| 7,809,399 B2 | 10/2010 | Lu | |
| 7,844,341 B2 | 11/2010 | Von Arx et al. | |
| 7,857,766 B2 | 12/2010 | Lasater et al. | |
| 7,899,526 B2 | 3/2011 | Benditt et al. | |
| 7,904,133 B2 | 3/2011 | Gehman et al. | |
| D639,437 S | 6/2011 | Bishay et al. | |
| 8,025,149 B2 | 9/2011 | Sterry et al. | |
| 8,036,731 B2 | 10/2011 | Kimchy et al. | |
| 8,036,748 B2 | 10/2011 | Zdeblick et al. | |
| 8,073,707 B2 | 12/2011 | Teller et al. | |
| 8,083,128 B2 | 12/2011 | Dembo et al. | |
| 8,123,576 B2 | 2/2012 | Kim | |
| 8,135,596 B2 | 3/2012 | Jung et al. | |
| 8,180,425 B2 | 5/2012 | Selvitelli et al. | |
| 8,200,320 B2 | 6/2012 | Kovacs | |
| 8,214,007 B2 | 7/2012 | Baker et al. | |
| 8,224,667 B1 | 7/2012 | Miller et al. | |
| 8,238,998 B2 | 8/2012 | Park | |
| 8,249,686 B2 | 8/2012 | Libbus et al. | |
| 8,258,962 B2 | 9/2012 | Robertson et al. | |
| 8,262,394 B2 | 9/2012 | Walker et al. | |
| 8,285,356 B2 | 10/2012 | Bly et al. | |
| 8,290,574 B2 | 10/2012 | Felid et al. | |
| 8,301,232 B2 | 10/2012 | Albert et al. | |
| 8,308,640 B2 | 11/2012 | Baldus et al. | |
| 8,315,687 B2 | 11/2012 | Cross et al. | |
| 8,369,936 B2 | 2/2013 | Farringdon et al. | |
| 8,386,009 B2 | 2/2013 | Lindberg et al. | |
| 8,389,003 B2 | 3/2013 | Mintchev et al. | |
| 8,404,275 B2 | 3/2013 | Habboushe | |
| 8,440,274 B2 | 5/2013 | Wang | |
| 8,514,086 B2 | 8/2013 | Harper et al. | |
| 8,542,123 B2 | 9/2013 | Robertson et al. | |
| 8,564,432 B2 | 10/2013 | Covannon et al. | |
| 8,583,227 B2 | 11/2013 | Savage et al. | |
| 8,597,186 B2 * | 12/2013 | Hafezi et al. | 600/302 |
| 8,668,645 B2 | 3/2014 | Drucker et al. | |
| 8,771,183 B2 | 7/2014 | Sloan | |
| 8,836,513 B2 | 9/2014 | Hafezi et al. | |
| 8,932,221 B2 | 1/2015 | Colliou et al. | |
| 8,945,005 B2 | 2/2015 | Hafezi et al. | |
| 2001/0027331 A1 | 10/2001 | Thompson | |
| 2001/0031071 A1 | 10/2001 | Nichols et al. | |
| 2001/0044588 A1 | 11/2001 | Mault | |
| 2001/0051766 A1 | 12/2001 | Gazdzinski | |
| 2001/0056262 A1 | 12/2001 | Cabiri et al. | |
| 2002/0002326 A1 | 1/2002 | Causey et al. | |
| 2002/0026111 A1 | 2/2002 | Ackerman | |
| 2002/0032384 A1 | 3/2002 | Raymond et al. | |
| 2002/0032385 A1 | 3/2002 | Raymond et al. | |
| 2002/0040278 A1 | 4/2002 | Anuzis et al. | |
| 2002/0067270 A1 | 6/2002 | Yarin et al. | |
| 2002/0077620 A1 | 6/2002 | Sweeney et al. | |
| 2002/0132226 A1 | 9/2002 | Nair | |
| 2002/0138009 A1 | 9/2002 | Brockway et al. | |
| 2002/0192159 A1 | 12/2002 | Reitberg | |
| 2002/0193669 A1 | 12/2002 | Glukhovsky | |
| 2002/0193846 A1 | 12/2002 | Pool et al. | |
| 2002/0198470 A1 | 12/2002 | Imran et al. | |
| 2003/0017826 A1 | 1/2003 | Fishman | |
| 2003/0023150 A1 | 1/2003 | Yokoi et al. | |
| 2003/0028226 A1 | 2/2003 | Thompson | |
| 2003/0063522 A1 | 4/2003 | Sagar | |
| 2003/0065536 A1 | 4/2003 | Hansen | |
| 2003/0076179 A1 | 4/2003 | Branch et al. | |
| 2003/0083559 A1 | 5/2003 | Thompson | |
| 2003/0126593 A1 | 7/2003 | Mault | |
| 2003/0130714 A1 | 7/2003 | Nielsen et al. | |
| 2003/0135128 A1 | 7/2003 | Suffin et al. | |
| 2003/0135392 A1 | 7/2003 | Vrijens et al. | |
| 2003/0152622 A1 | 8/2003 | Louie-Helm et al. | |
| 2003/0158466 A1 | 8/2003 | Lynn et al. | |
| 2003/0158756 A1 | 8/2003 | Abramson | |
| 2003/0162556 A1 | 8/2003 | Libes | |
| 2003/0164401 A1 | 9/2003 | Andreasson et al. | |
| 2003/0167000 A1 | 9/2003 | Mullick et al. | |
| 2003/0171791 A1 | 9/2003 | KenKnight | |
| 2003/0171898 A1 | 9/2003 | Tarassenko et al. | |
| 2003/0181788 A1 | 9/2003 | Yokoi et al. | |
| 2003/0181815 A1 | 9/2003 | Ebner et al. | |
| 2003/0185286 A1 | 10/2003 | Yuen | |
| 2003/0187337 A1 | 10/2003 | Tarassenko et al. | |
| 2003/0187338 A1 | 10/2003 | Say et al. | |
| 2003/0195403 A1 | 10/2003 | Berner et al. | |
| 2003/0213495 A1 | 11/2003 | Fujita et al. | |
| 2003/0214579 A1 | 11/2003 | Iddan | |
| 2003/0216622 A1 | 11/2003 | Meron et al. | |
| 2003/0216625 A1 | 11/2003 | Phipps | |
| 2003/0216666 A1 | 11/2003 | Ericson et al. | |
| 2003/0216729 A1 | 11/2003 | Marchitto | |
| 2003/0229382 A1 | 12/2003 | Sun et al. | |
| 2003/0232895 A1 | 12/2003 | Omidian et al. | |
| 2004/0008123 A1 | 1/2004 | Carrender et al. | |
| 2004/0018476 A1 | 1/2004 | LaDue | |
| 2004/0019172 A1 | 1/2004 | Yang et al. | |
| 2004/0034295 A1 | 2/2004 | Salganicoff | |
| 2004/0049245 A1 | 3/2004 | Gass | |
| 2004/0073095 A1 | 4/2004 | Causey et al. | |
| 2004/0073454 A1 | 4/2004 | Urquhart et al. | |
| 2004/0077995 A1 | 4/2004 | Ferek-Petric | |
| 2004/0082982 A1 | 4/2004 | Gord et al. | |
| 2004/0087839 A1 | 5/2004 | Raymond et al. | |
| 2004/0092801 A1 | 5/2004 | Drakulic | |
| 2004/0106859 A1 | 6/2004 | Say et al. | |
| 2004/0111011 A1 | 6/2004 | Uchiyama et al. | |

(56) References Cited

U.S. PATENT DOCUMENTS

| | | |
|---|---|---|
| 2004/0115507 A1 | 6/2004 | Potter et al. |
| 2004/0115517 A1 | 6/2004 | Fukuda et al. |
| 2004/0121015 A1 | 6/2004 | Chidlaw et al. |
| 2004/0122297 A1 | 6/2004 | Stahmann et al. |
| 2004/0138558 A1 | 7/2004 | Dunki-Jacobs et al. |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167801 A1 | 8/2004 | Say et al. |
| 2004/0171914 A1 | 9/2004 | Avni |
| 2004/0193020 A1 | 9/2004 | Chiba |
| 2004/0193029 A1 | 9/2004 | Glukhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0258571 A1 | 12/2004 | Lee et al. |
| 2004/0260154 A1 | 12/2004 | Sidelnik |
| 2004/0267240 A1 | 12/2004 | Gross et al. |
| 2005/0017841 A1 | 1/2005 | Doi |
| 2005/0020887 A1 | 1/2005 | Goldberg |
| 2005/0021103 A1 | 1/2005 | DiLorenzo |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0055014 A1 | 3/2005 | Coppeta et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0075145 A1 | 4/2005 | Dvorak et al. |
| 2005/0090753 A1 | 4/2005 | Goor et al. |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0137480 A1 | 6/2005 | Alt et al. |
| 2005/0143623 A1 | 6/2005 | Kojima |
| 2005/0146594 A1 | 7/2005 | Nakatani et al. |
| 2005/0148883 A1 | 7/2005 | Boesen |
| 2005/0151625 A1 | 7/2005 | Lai |
| 2005/0154277 A1 | 7/2005 | Tang et al. |
| 2005/0154428 A1 | 7/2005 | Bruinsma |
| 2005/0156709 A1 | 7/2005 | Gilbert et al. |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0245839 A1 | 11/2005 | Stivoric et al. |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0280539 A1 | 12/2005 | Pettus |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0074283 A1 | 4/2006 | Henderson |
| 2006/0074319 A1 | 4/2006 | Barnes et al. |
| 2006/0078765 A1 | 4/2006 | Yang et al. |
| 2006/0089858 A1 | 4/2006 | Ling |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122667 A1 | 6/2006 | Chavan et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0158820 A1 | 7/2006 | Takiguchi |
| 2006/0161225 A1 | 7/2006 | Sormann et al. |
| 2006/0179949 A1 | 8/2006 | Kim |
| 2006/0183992 A1 | 8/2006 | Kawashima |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0229053 A1 | 10/2006 | Sivard |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253005 A1 | 11/2006 | Drinan |
| 2006/0255064 A1 | 11/2006 | Donaldson |
| 2006/0265246 A1 | 11/2006 | Hoag |
| 2006/0267774 A1 | 11/2006 | Feinberg et al. |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0285607 A1 | 12/2006 | Strodtbeck et al. |
| 2006/0287693 A1 | 12/2006 | Kraft et al. |
| 2006/0289640 A1 | 12/2006 | Mercure |
| 2006/0293607 A1 | 12/2006 | Alt |
| 2007/0000776 A1 | 1/2007 | Karube et al. |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0066929 A1 | 3/2007 | Ferren et al. |
| 2007/0073353 A1 | 3/2007 | Rooney et al. |
| 2007/0088194 A1 | 4/2007 | Tahar |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135691 A1 | 6/2007 | Zingelewicz et al. |
| 2007/0135803 A1 | 6/2007 | Belson |
| 2007/0142721 A1 | 6/2007 | Berner et al. |
| 2007/0156016 A1 | 7/2007 | Betesh |
| 2007/0160789 A1 | 7/2007 | Merical |

(56) References Cited

U.S. PATENT DOCUMENTS

| | | |
|---|---|---|
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0179371 A1 | 8/2007 | Peyser et al. |
| 2007/0180047 A1 | 8/2007 | Dong et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0207858 A1 | 9/2007 | Breving |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0244810 A1 | 10/2007 | Rudolph |
| 2007/0249946 A1 | 10/2007 | Kumar et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0291715 A1 | 12/2007 | Laroia et al. |
| 2007/0299480 A1 | 12/2007 | Hill |
| 2008/0004503 A1 | 1/2008 | Nisani et al. |
| 2008/0014866 A1 | 1/2008 | Lipowski |
| 2008/0015421 A1 | 1/2008 | Penner |
| 2008/0015494 A1 | 1/2008 | Santini et al. |
| 2008/0015893 A1 | 1/2008 | Miller et al. |
| 2008/0020037 A1 | 1/2008 | Robertson et al. |
| 2008/0021519 A1 | 1/2008 | De Geest |
| 2008/0021521 A1 | 1/2008 | Shah |
| 2008/0027679 A1 | 1/2008 | Shklarski |
| 2008/0033273 A1 | 2/2008 | Zhou |
| 2008/0033301 A1 | 2/2008 | Dellavecchia et al. |
| 2008/0038588 A1 | 2/2008 | Lee |
| 2008/0039700 A1 | 2/2008 | Drinan et al. |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0051767 A1 | 2/2008 | Rossing et al. |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Boric-Lubecke |
| 2008/0077028 A1 | 3/2008 | Schaldach et al. |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0099366 A1 | 5/2008 | Niemiec et al. |
| 2008/0103440 A1 | 5/2008 | Ferren et al. |
| 2008/0112885 A1 | 5/2008 | Okunev et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Marholev |
| 2008/0139907 A1 | 6/2008 | Rao et al. |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBoeuf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214903 A1 | 9/2008 | Orbach |
| 2008/0214985 A1 | 9/2008 | Yanaki |
| 2008/0223936 A1 | 9/2008 | Mickle et al. |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0281636 A1 | 11/2008 | Jung et al. |
| 2008/0284599 A1* | 11/2008 | Zdeblick et al. ............ 340/572.1 |
| 2008/0288026 A1 | 11/2008 | Cross et al. |
| 2008/0288027 A1 | 11/2008 | Kroll |
| 2008/0294020 A1 | 11/2008 | Sapounas |
| 2008/0299197 A1 | 12/2008 | Toneguzzo et al. |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0306362 A1 | 12/2008 | Davis |
| 2008/0311852 A1 | 12/2008 | Hansen |
| 2008/0312522 A1 | 12/2008 | Rowlandson |
| 2008/0316020 A1 | 12/2008 | Robertson |
| 2009/0006133 A1 | 1/2009 | Weinert |
| 2009/0009330 A1 | 1/2009 | Sakama et al. |
| 2009/0009332 A1 | 1/2009 | Nunez et al. |
| 2009/0024045 A1 | 1/2009 | Prakash |
| 2009/0024112 A1 | 1/2009 | Edwards et al. |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0076340 A1 | 3/2009 | Libbus et al. |
| 2009/0076343 A1 | 3/2009 | James |
| 2009/0076397 A1 | 3/2009 | Libbus et al. |
| 2009/0082645 A1 | 3/2009 | Hafezi et al. |
| 2009/0087483 A1 | 4/2009 | Sison |
| 2009/0088618 A1 | 4/2009 | Arneson |
| 2009/0099435 A1 | 4/2009 | Say et al. |
| 2009/0105561 A1 | 4/2009 | Boyden et al. |
| 2009/0110148 A1 | 4/2009 | Zhang |
| 2009/0112626 A1 | 4/2009 | Talbot |
| 2009/0124871 A1 | 5/2009 | Arshak |
| 2009/0131774 A1 | 5/2009 | Sweitzer |
| 2009/0134181 A1 | 5/2009 | Wachman et al. |
| 2009/0135886 A1 | 5/2009 | Robertson et al. |
| 2009/0142853 A1 | 6/2009 | Warrington et al. |
| 2009/0149839 A1 | 6/2009 | Hyde et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182207 A1 | 7/2009 | Riskey et al. |

(56) References Cited

U.S. PATENT DOCUMENTS

| | | |
|---|---|---|
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0227988 A1 | 9/2009 | Wood et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0247836 A1 | 10/2009 | Cole et al. |
| 2009/0253960 A1 | 10/2009 | Takenaka |
| 2009/0256702 A1* | 10/2009 | Robertson et al. ....... 340/539.12 |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0277815 A1 | 11/2009 | Kohl et al. |
| 2009/0281539 A1 | 11/2009 | Selig |
| 2009/0292194 A1 | 11/2009 | Libbus et al. |
| 2009/0295548 A1 | 12/2009 | Ronkka |
| 2009/0296677 A1 | 12/2009 | Mahany |
| 2009/0301925 A1 | 12/2009 | Alloro et al. |
| 2009/0303920 A1 | 12/2009 | Mahany |
| 2009/0306633 A1 | 12/2009 | Trovato et al. |
| 2009/0312619 A1 | 12/2009 | Say et al. |
| 2009/0318303 A1 | 12/2009 | Delamarche et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0001841 A1 | 1/2010 | Cardullo |
| 2010/0006585 A1 | 1/2010 | Flowers et al. |
| 2010/0010330 A1 | 1/2010 | Rankers |
| 2010/0033324 A1 | 2/2010 | Shimizu et al. |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0081894 A1* | 4/2010 | Zdeblick et al. .............. 600/302 |
| 2010/0082367 A1 | 4/2010 | Hains et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0106001 A1 | 4/2010 | Say et al. |
| 2010/0118853 A1 | 5/2010 | Godfrey |
| 2010/0139672 A1 | 6/2010 | Kroll et al. |
| 2010/0160742 A1 | 6/2010 | Seidl et al. |
| 2010/0168659 A1 | 7/2010 | Say et al. |
| 2010/0179398 A1 | 7/2010 | Say et al. |
| 2010/0185055 A1 | 7/2010 | Robertson |
| 2010/0191073 A1 | 7/2010 | Tarassenko et al. |
| 2010/0203394 A1* | 8/2010 | Bae et al. ...................... 429/246 |
| 2010/0210299 A1 | 8/2010 | Gorbachov |
| 2010/0222652 A1 | 9/2010 | Cho |
| 2010/0228113 A1 | 9/2010 | Solosko |
| 2010/0233026 A1 | 9/2010 | Ismagliov et al. |
| 2010/0234706 A1 | 9/2010 | Gilland |
| 2010/0234715 A1 | 9/2010 | Shin |
| 2010/0234914 A1 | 9/2010 | Shen |
| 2010/0245091 A1 | 9/2010 | Singh |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0268288 A1 | 10/2010 | Hunter et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0295694 A1 | 11/2010 | Kauffman et al. |
| 2010/0298668 A1 | 11/2010 | Hafezi et al. |
| 2010/0298730 A1 | 11/2010 | Tarassenko et al. |
| 2010/0299155 A1 | 11/2010 | Findlay et al. |
| 2010/0312188 A1 | 12/2010 | Robertson et al. |
| 2010/0312577 A1 | 12/2010 | Goodnow et al. |
| 2010/0312580 A1 | 12/2010 | Tarassenko et al. |
| 2010/0332443 A1 | 12/2010 | Gartenberg |
| 2011/0004079 A1 | 1/2011 | Al-Ali et al. |
| 2011/0009715 A1 | 1/2011 | O'Reilly et al. |
| 2011/0029622 A1 | 2/2011 | Walker et al. |
| 2011/0040203 A1 | 2/2011 | Savage et al. |
| 2011/0050431 A1 | 3/2011 | Hood et al. |
| 2011/0054265 A1 | 3/2011 | Hafezi et al. |
| 2011/0065983 A1 | 3/2011 | Hafezi et al. |
| 2011/0077660 A1 | 3/2011 | Janik et al. |
| 2011/0081860 A1 | 4/2011 | Brown et al. |
| 2011/0105864 A1 | 5/2011 | Robertson et al. |
| 2011/0124983 A1 | 5/2011 | Kroll et al. |
| 2011/0144470 A1 | 6/2011 | Mazar et al. |
| 2011/0224912 A1 | 9/2011 | Bhavaraju et al. |
| 2011/0230732 A1 | 9/2011 | Edman et al. |
| 2011/0237924 A1 | 9/2011 | McGusty et al. |
| 2011/0270112 A1 | 11/2011 | Manera et al. |
| 2011/0279963 A1 | 11/2011 | Kumar et al. |
| 2012/0024889 A1* | 2/2012 | Robertson et al. .............. 222/23 |
| 2012/0029309 A1 | 2/2012 | Paquet et al. |
| 2012/0062371 A1 | 3/2012 | Radivojevic et al. |
| 2012/0083715 A1 | 4/2012 | Yuen et al. |
| 2012/0089000 A1 | 4/2012 | Bishay et al. |
| 2012/0101396 A1 | 4/2012 | Solosko et al. |
| 2012/0197144 A1 | 8/2012 | Christ et al. |
| 2012/0214140 A1 | 8/2012 | Brynelsen et al. |
| 2012/0265544 A1 | 10/2012 | Hwang et al. |
| 2012/0299723 A1 | 11/2012 | Hafezi et al. |

(56) References Cited

U.S. PATENT DOCUMENTS

| | | |
|---|---|---|
| 2012/0310070 A1 | 12/2012 | Kumar et al. |
| 2012/0316413 A1 | 12/2012 | Liu et al. |
| 2013/0030259 A1 | 1/2013 | Thomsen et al. |
| 2013/0057385 A1 | 3/2013 | Murakami et al. |
| 2013/0060115 A1 | 3/2013 | Gehman et al. |
| 2014/0315170 A1 | 10/2014 | Ionescu et al. |
| 2014/0334575 A1 | 11/2014 | Arne et al. |
| 2015/0048929 A1 | 2/2015 | Robertson et al. |
| 2015/0051465 A1 | 2/2015 | Robertson et al. |
| 2015/0080677 A1 | 3/2015 | Thompson et al. |
| 2015/0080678 A1 | 3/2015 | Frank et al. |
| 2015/0080679 A1 | 3/2015 | Frank et al. |
| 2015/0080680 A1 | 3/2015 | Zdeblick et al. |
| 2015/0080681 A1 | 3/2015 | Hafezi et al. |
| 2015/0127737 A1 | 5/2015 | Thompson et al. |
| 2015/0127738 A1 | 5/2015 | Thompson et al. |
| 2015/0149375 A1 | 5/2015 | Thompson et al. |

FOREIGN PATENT DOCUMENTS

| | | |
|---|---|---|
| CN | 101005470 | 7/2007 |
| DE | 10313005 | 10/2004 |
| EP | 0344939 | 12/1989 |
| EP | 1246356 | 10/2002 |
| EP | 1342447 | 9/2003 |
| EP | 1534054 | 5/2005 |
| EP | 1702553 | 9/2006 |
| EP | 2143369 | 1/2010 |
| GB | 775071 | 5/1957 |
| GB | 2432862 | 6/2007 |
| IL | 172917 | 6/2010 |
| JP | 61017949 | 1/1986 |
| JP | 61072712 | 4/1986 |
| JP | 05-228128 | 9/1993 |
| JP | H0646539 | 2/1994 |
| JP | 09-330159 | 12/1997 |
| JP | 10-14898 | 1/1998 |
| JP | 2000-506410 | 5/2000 |
| JP | 2002-224053 | 8/2002 |
| JP | 2002263185 | 9/2002 |
| JP | 2002282219 | 10/2002 |
| JP | 2002291684 | 10/2002 |
| JP | 2004-7187 | 1/2004 |
| JP | 2004134384 | 4/2004 |
| JP | 2004313242 | 11/2004 |
| JP | 2005-073886 | 3/2005 |
| JP | 2005-087552 | 4/2005 |
| JP | 2005-304880 | 4/2005 |
| JP | 2005124708 | 5/2005 |
| JP | 2005-532841 | 11/2005 |
| JP | 2005-532849 | 11/2005 |
| JP | 2006006377 | 1/2006 |
| JP | 2006509574 | 3/2006 |
| JP | 2006-177699 | 7/2006 |
| JP | 2006-187611 | 7/2006 |
| JP | 2006278091 | 10/2006 |
| JP | 2006346000 | 12/2006 |
| JP | 3876573 | 1/2007 |
| JP | 2007159631 | 6/2007 |
| JP | 2007-313340 | 12/2007 |
| JP | 2007-330677 | 12/2007 |
| JP | 2008011865 | 1/2008 |
| JP | 2008501415 | 1/2008 |
| JP | 2008191955 | 8/2008 |
| JP | 2009-061236 | 3/2009 |
| KR | 20020015907 | 3/2002 |
| KR | 20020061744 | 7/2002 |
| KR | 200609977523 | 7/2006 |
| KR | 927471 | 11/2009 |
| KR | 10-2012-09995 | 9/2012 |
| TW | 200301864 | 7/2003 |
| TW | 553735 | 9/2003 |
| TW | 200724094 | 7/2007 |
| WO | WO8802237 | 4/1988 |
| WO | WO9221307 | 12/1992 |
| WO | WO9308734 | 5/1993 |
| WO | WO9319667 | 10/1993 |
| WO | WO9401165 | 1/1994 |
| WO | WO9516393 | 6/1995 |
| WO | WO9714112 | 4/1997 |
| WO | WO9739963 | 10/1997 |
| WO | WO9843537 | 10/1998 |
| WO | WO9937290 | 7/1999 |
| WO | WO9959465 | 11/1999 |
| WO | WO0033246 | 6/2000 |
| WO | WO0100085 | 1/2001 |
| WO | WO0147466 | 7/2001 |
| WO | WO0149364 | 7/2001 |
| WO | WO0174011 | 10/2001 |
| WO | WO0180731 | 11/2001 |
| WO | WO0235997 | 5/2002 |
| WO | WO0245489 | 6/2002 |
| WO | WO02058330 | 7/2002 |
| WO | WO02062276 | 8/2002 |
| WO | WO02087681 | 11/2002 |
| WO | WO02095351 | 11/2002 |
| WO | WO03005877 | 1/2003 |
| WO | WO03050643 | 6/2003 |
| WO | WO03068061 | 8/2003 |
| WO | WO2004014225 | 2/2004 |
| WO | WO2004019172 | 3/2004 |
| WO | WO2004039256 | 5/2004 |
| WO | WO2004059551 | 7/2004 |
| WO | WO2004066833 | 8/2004 |
| WO | WO2004066834 | 8/2004 |
| WO | WO2004066903 | 8/2004 |
| WO | WO2004068748 | 8/2004 |
| WO | WO2004068881 | 8/2004 |
| WO | WO2004075751 | 9/2004 |
| WO | WO2004109316 | 12/2004 |
| WO | WO2004110555 | 12/2004 |
| WO | WO2005011237 | 2/2005 |
| WO | WO2005020023 | 3/2005 |
| WO | WO2005024687 | 3/2005 |
| WO | WO2005041767 | 5/2005 |
| WO | WO2005047837 | 5/2005 |
| WO | WO2005051166 | 6/2005 |
| WO | WO2005053517 | 6/2005 |
| WO | WO2005082436 | 9/2005 |
| WO | WO2005083621 | 9/2005 |
| WO | WO2005110238 | 11/2005 |
| WO | WO2005117697 | 12/2005 |
| WO | WO2006009404 | 1/2006 |
| WO | WO2006021932 | 3/2006 |
| WO | WO2006027586 | 3/2006 |
| WO | WO2006028347 | 3/2006 |
| WO | WO2006035351 | 4/2006 |
| WO | WO2006037802 | 4/2006 |
| WO | WO2006046648 | 5/2006 |
| WO | WO2006055892 | 5/2006 |
| WO | WO2006055956 | 5/2006 |
| WO | WO2006059338 | 6/2006 |
| WO | WO2006075016 | 7/2006 |
| WO | WO2006100620 | 9/2006 |
| WO | WO2006104843 | 10/2006 |
| WO | WO2006109072 | 10/2006 |
| WO | WO2006116718 | 11/2006 |
| WO | WO2006119345 | 11/2006 |
| WO | WO2006127355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |

(56) References Cited

FOREIGN PATENT DOCUMENTS

| | | |
|---|---|---|
| WO | WO2007096810 | 8/2007 |
| WO | WO2007101141 | 9/2007 |
| WO | WO2007115087 | 10/2007 |
| WO | WO2007120946 | 10/2007 |
| WO | WO2007127316 | 11/2007 |
| WO | WO2007127879 | 11/2007 |
| WO | WO2007127945 | 11/2007 |
| WO | WO2007128165 | 11/2007 |
| WO | WO2007130491 | 11/2007 |
| WO | WO2007133526 | 11/2007 |
| WO | WO2007143535 | 12/2007 |
| WO | WO2007149546 | 12/2007 |
| WO | WO2008008281 | 1/2008 |
| WO | WO2008012700 | 1/2008 |
| WO | WO2008030482 | 3/2008 |
| WO | WO2008039030 | 4/2008 |
| WO | WO2008052136 | 5/2008 |
| WO | WO2008061138 | 5/2008 |
| WO | WO2008063626 | 5/2008 |
| WO | WO2008066617 | 6/2008 |
| WO | WO2008076464 | 6/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009001108 | 12/2008 |
| WO | WO2009005759 | 1/2009 |
| WO | WO2009006615 | 1/2009 |
| WO | WO2009022343 | 2/2009 |
| WO | WO2009029453 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010000085 | 1/2010 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010075115 | 7/2010 |
| WO | WO2010080765 | 7/2010 |
| WO | WO2010080843 | 7/2010 |
| WO | WO2010107563 | 9/2010 |
| WO | WO2010115194 | 10/2010 |
| WO | WO2010132331 | 11/2010 |
| WO | WO2010135516 | 11/2010 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |
| WO | WO2012104657 | 8/2012 |
| WO | WO2012158190 | 11/2012 |
| WO | WO2013012869 | 1/2013 |

OTHER PUBLICATIONS

Arshak et al., A Review and Adaptation of Methods of Object Tracking to Telemetry Capsules IC-Med (2007) vol. 1, No. 1, Issue 1, pp. 35 of 46.
"ASGE Technology Status Evaluation Report: wireless capsule endoscopy" American Soc. for Gastrointestinal Endoscopy (2006) vol. 63, No. 4; 7 pages.
Aydin et al., "Design and implementation considerations for an advanced wireless interface in miniaturized integrated sensor Microsystems" Sch. of Eng. & Electron., Edinburgh Univ., UK; (2003); abstract.
Barrie, Heidelberg pH capsule gastric analysis. Texbook of Natural Medicine, (1992), Pizzorno, Murray & Barrie.
Bohidar et al., "Dielectric Behavior of Gelatin Solutions and Gels" Colloid Polym Sci (1998) 276:81-86.
Brock, "Smart Medicine: The Application of Auto-ID Technology to Healthcare" Auto-ID Labs (2002) http://www.autoidlabs.org/uploads/media/MIT-AUTOID-WH-010.pdf.
Carlson et al., "Evaluation of a non-invasive respiratory monitoring system for sleeping subjects" Physiological Measurement (1999) 20(1): 53.
Coury, L. "Conductance Measurement Part 1: Theory"; Current Separations, 18:3 (1999) p. 91-96.
Delvaux et al., "Capsule endoscopy: Technique and indications" Clinical Gastoenterology (2008) vol. 22, Issue 5, pp. 813-837.
Dhar et al., "Electroless nickel plated contacts on porous silicon" Appl. Phys. Lett. 68 (10) pp. 1392-1393 (1996).
Eldek A., "Design of double dipole antenna with enhanced usable bandwidth for wideband phased array applications" Progress in Electromagnetics Research PIER 59, 1-15 (2006).
Fawaz et al., "Enhanced Telemetry System using CP-QPSK Band—Pass Modulation Technique Suitable for Smart Pill Medical Application" IFIP IEEE Dubai Conference (2008); http://www.asic.fh-offenburg.de/downloads/ePille/IFIP_IEEE_Dubai_Conference.pdf.
Ferguson et al., "Dialectric Constant Studies III Aqueous Gelatin Solutions" J. Chem. Phys. 2, 94 (1934) p. 94-98.
Furse C. M., "Dipole Antennas" J. Webster (ed). Wiley Encyclopedia of Electrical and Electronics Engineering (1999) p. 575-581.
Gilson, D.R. "Molecular dynamics simulation of dipole interactions", Department of Physics, Hull University, Dec. (2002), p. 1-43.
Given Imaging, "Agile Patency Brochure" (2006) http://www.inclino.no/documents/AgilePatencyBrochure_Global_GMB-0118-01.pdf; 4pp.
Gonzalez-Guillaumin et al., "Ingestible capsule for impedance and pH monitoring in the esophagus" IEEE Trans Biomed Eng. (2007) 54(12): 2231-6; abstract.
Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html.
Heydari et al., "Analysis of the PLL jitter due to power/ground and substrate noise"; IEEE Transactions on Circuits and Systems (2004) 51(12): 2404-16.
ISFET—Ion Sensitive Field-Effect Transistor; MICROSENS S.A. pdf document. Office Action dated Jun. 13, 2011 for U.S. Appl. No. 12/238,345; 4pp.
INTROMEDIC, MicroCam Innovative Capsule Endoscope Pamphlet. (2006) 8 pp (http://www.intromedic.com/en/product/productinfo.asp).
Juvenile Diabetes Research Foundation International (JDRF), "Artificial Pancreas Project" (2010); http://www.artificialpancreasproject.com/; 3 pp.
Kamada K., "Electrophoretic deposition assisted by soluble anode" Materials Letters 57 (2003) 2348-2351.
Li, P-Y, et al. "An electrochemical intraocular drug delivery device", Sensors and Actuators A 143 (2008) p. 41-48.
LIFESCAN, "OneTouch UltraLink™" http://www.lifescan.com/products/meters/ultralink (2010) 2 pp.
MacKay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.
Mackay et al., "Endoradiosonde" Nature, (1957) 1239-1240, 179 Nature Publishing Group.
McKenzie et al., "Validation of a new telemetric core temperature monitor" J. Therm. Biol. (2004) 29(7-8):605-11.

(56) References Cited

OTHER PUBLICATIONS

Medtronic, "CareLink Therapy Management Software for Diabetes" (2010); https://carelink.minimed.com/patient/entry.jsp?bhcp=1; 1 pp.

Medtronic, "Carelink™ USB" (2008) http://www.medtronicdiabetes.com/pdf/carelink_usb_factsheet.pdf 2pp.

Medtronic "The New MiniMed Paradigm® REAL-Time Revel™ System" (2010) http://www.medtronicdiabetes.com/products/index.html; 2 pp.

Medtronic, "Mini Med Paradigm® Revel™ Insulin Pump" (2010) http://www.medtronicdiabetes.com/products/insulinpumps/index.html; 2 pp.

Medtronic, Mini Med Paradigm™ Veo™ System: Factsheet (2010). http://www.medtronic-diabetes.com.au/downloads/Paradigm%20Veo%20Factsheet.pdf ; 4 pp.

Melanson, "Walkers swallow RFID pills for science" Engadget (2008); http://www.engadget.com/2008/07/29/walkers-swallow-rfid-pills-for-science/.

MINIMITTER Co. Inc. "Actiheart" Traditional 510(k) Summary. Sep. 27, 2005.

MINIMITTER Co. Inc. Noninvasive technology to help your studies succeed. MiniMitter.com Mar. 31, 2009.

MINI MITTER Co, Inc. 510(k) Premarket Notification Mini-Logger for Diagnostic Spirometer. Sep. 21, 1999.

MINI MITTER Co, Inc. 510(k) Premarket Notification for VitalSense. Apr. 22, 2004.

MINIMITTER Co. Inc. VitalSense Integrated Physiological Monitoring System. Product Description. (2005).

MINIMITTER Co. Inc. VitalSense Wireless Vital Signs Monitoring. Temperatures.com Mar. 31, 2009.

Mohaverian et al., "Estimation of gastric residence time of the Heidelberg capsule in humans: effect of varying food composition" Gastroenterology (1985) 89:(2): 392-7.

"New 'smart pill' to track adherence" E-Health-lnsider (2010) http://www.e-health-insider.com/news/5910/new_'smart_pill'_monitors_medicines.

NPL_AntennaBasics.pdf, Radio Antennae, http://www.erikdeman.de/html/sail018h.htm; (2008) 3pp.

O'Brien et al., "The Production and Characterization of Chemically Reactive Porous Coatings of Zirconium Via Unbalanced Magnetron Sputtering" Surface and Coatings Technology (1996) 86-87; 200-206.

Park, "Medtronic to Buy MiniMed for $3.7 Billion" (2001) HomeCare; http://homecaremag.com/mag/medical_medtronic_buy_minimed/; 2 pp.

Philips Respironics (http/minimitter.com/products.cfm) Products, Noninvasive Technology to Help Your Studies Succeed. 510(k) Permanent Notification for Vital Sense. Apr. 22, 2004.

"RFID "pill" monitors marchers" RFID News (2008) http://www.rfidnews.org/2008/07/23/rfid-pill-monitors-marchers/.

Roulstone, et al., "Studies on Polymer Latex Films: I. A study of latex film morphology" Polymer International 24 (1991) pp. 87-94.

Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.

Santini, J.T. et al, "Microchips as controlled drug delivery-devices", Agnew. Chem. Int. Ed. (2000), vol. 39, p. 2396-2407.

"SensiVida minimally invasive clinical systems" Investor Presentation Oct. 2009 28pp; http://www.sensividamedtech.com/SensiVidaGeneralOctober09.pdf.

Shawgo, R.S. et al. "BioMEMS from drug delivery", Current Opinion in Solid State and Material Science 6 (2002), p. 329-334.

Shin et al., "A Simple Route to Metal Nanodots and Nanoporous Metal Films"; Nano Letters, vol. 2, No. 9 (2002) pp. 933-936.

Shrivas et al., "A New Platform for Bioelectronics-Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010.

"Smartlife awarded patent for knitted transducer" Innovation in Textiles News: http://www.innovationintextiles.com/articles/208.php; 2pp. (2009).

"The SmartPill Wireless Motility Capsule" SmartPill, The Measure of GI Health; (2010) http://www.smartpillcorp.com/index.cfm?pagepath=Products/The_SmartPill_Capsule&id=17814.

Solanas et al., "RFID Technology for the Health Care Sector" Recent Patents on Electrical Engineering (2008) 1, 22-31.

Soper, S.A. et al. "Bio-Mems Technologies and Applications", Chapter 12, "MEMS for Drug Delivery", p. 325-346 (2007).

Swedberg, "University Team Sees Ingestible RFID Tag as a Boon to Clinical Trials" RFID Journal Apr. 27, 2010; http://www.rfidjournal.com/article/view/7560/1.

Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.

Tatbul et al., "Confidence-based data management for personal area sensor networks" ACM International Conference Proceeding Series (2004) 72.

Tierney, M.J. et al "Electroreleasing Composite Membranes for Delivery of Insulin and other Biomacromolecules", J. Electrochem. Soc., vol. 137, No. 6, Jun. 1990, p. 2005-2006.

University of Florida News "Rx for health: Engineers design pill that signals it has been swallowed" (2010) 2pp.; http://news.ufl.edu/2010/03/31/antenna-pill-2/.

U.S. Appl. No. 12/238,345, filed Sep. 25, 2008, Hooman et al., Non-Final Office Action mailed Jun. 13, 2011 22pp.

Walkey, "MOSFET Structure and Processing"; 97.398* Physical Electronics Lecture 20; Office Action dated Jun. 13, 2011 for U.S. Appl. No. 12/238,345; 24 pp.

Watson, et al., "Determination of the relationship between the pH and conductivity of gastric juice" Physiol Meas. 17 (1996) pp. 21-27.

Wongmanerod et al., "Determination of pore size distribution and surface area of thin porous silicon layers by spectroscopic ellipsometry" Applied Surface Science 172 (2001) 117-125.

Xiaoming et al., "A telemedicine system for wireless home healthcare based on bluetooth and the internet" Telemedicine Journal and e-health (2004) 10(S2): S110-6.

Yang et al., "Fast-switching frequency synthesizer with a discriminator-aided phase detector" IEEE Journal of Solid-State Circuits (2000) 35(10): 1445-52.

Yao et al., "Low Power Digital Communication in Implantable Devices Using Volume Conduction of Biological Tissues" Proceedings of the 28th IEEE, EMBS Annual International Conference, Aug. 30-Sep. 3, 2006.

Zimmerman, "Personal Area Networks: Near-field intrabody communication" IBM Systems Journal (1996) 35 (3-4):609-17.

Description of ePatch Technology Platform for ECG and EMG, located it http://www.madebydelta.com/imported/images/DELTA_Web/documents/ME/ePatch_ECG_EMG.pdf, dated Sep. 2, 2010.

Zworkin, "A Radio Pill" Nature, (1957) 898, 179 Nature Publishing Group.

Hotz "The Really Smart Phone" The Wall Street Journal, What They Know (2011); 6 pp.; http://online.wsj.com/article/SB10001424052748704547604576263261679848814.html?mod=djemTECH_t.

"The SmartPill Wireless Motility Capsule" SmartPill, The Measure of GI Health; (2010) http://www.smartpillcorp.com/index.cfm?pagepath=Products/The_SmartPill_Capsule &id=17814.

Gaglani S. "Put Your Phone, or Skin, on Vibrate" MedGadget (2012) http://medgadget.com/2012/03/put-your-phone-or-skin-on-vibrate.html 8pp.

Jimbo et al., "Gastric-fluid-utilized micro battery for micro medical devices" The Sixth International Workshop on Micro and Nanotechnology for Power Geneartion and Energy Conservation Applications, (2006) pp. 97-100.

Rolison et al., "Electrically conductive oxide aerogels: new materials in electrochemistry" J. Mater. Chem. (2001) 1, 963-980.

Shrivas et al., "A New Platform for Bioelectronics-Electronic Pill", Cummins College, (2010).

(56) References Cited

OTHER PUBLICATIONS

Halthion Medical Technologies "Providing Ambulatory Medical Devices Which Monitor, Measure and Record" webpage. Online website: http://www.halthion.com/; downloaded May 30, 2012.

Hoeksma, J. "New 'smart pill' to track adherence" E-Health-Insider May (2010) http://www.e-health-insidercom/news/5910/new_'smart_pill'_monitors_medicines.

Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.

Platt, D., "Modulation and Deviation" AE6EO, Foothills Amateur Radio Society; Oct. 26, 2007; 61 pp.

Evanczuk, S., "PIC MCU software library uses human body for secure communications link" EDN Network; edn.com; Feb. 26, 2013 Retrieved from internet Jun. 19, 2013 at http://www.edn.com/electronics-products/other/4407842/PIC-MCU-software-library-uses-human-body-for-secure-communications-link; 5 pp.

"PALO Bluetooth Baseband" PALO Bluetooth Resource Center (2002) Retrieved from internet Dec. 12, 2012 at URL: http://palowireless.com/bluearticles/baseband.asp; Office Action dated Jan. 17, 2013 for EP08853901.0.

Trutag, Technologies, Inc., Spectral Microtags for Authentication and Anti-Counterfeiting; "Product Authentication and Brand Protection Solutions"; http://www.trutags.com/; downloaded Feb. 12, 2013; 1 pp.

Lin et al., "Do Physiological Data Relate to Traditional Usability Indexes?" Proceedings of OZCHI 2005, Canberra, Australia (2005) 10 pp.

Mandryk et al., "A physiological approach for continuously modeling user emotion in interactive play environments" Proceedings of Measuring Behavior (2008) (Maastrichtm The Netherlandsm Aug. 26-29) 2 pp.

Mandryk et al., "Objectively Evaluating Entertainment Technology" Simon Fraser University; CHI (2004) ACM 1-58113-703-6/04/0004; 2 pp.

Baskiyar, S. "A Real-time Fault Tolerant Intra-body Network" Dept. of Comp. Sci & Soft Eng; Auburn University; Proceedings of the 27th Annual IEEE Conference; 0742-1303/02 (2002) IEEE; 6 pp.

Owano, N., "Study proposes smart sutures with sensors for wounds" Phys.Org. Aug. (2012). http://phys.org/news/2012-08-smart-sutures-sensors-wounds.html.

Winter, J. et al. "The material properties of gelatin gels"; USA Ballistic Research Laboratories, Mar. (1975), p. 1-157.

Kim et al., "A Semi-Interpenetrating Network System for a Polymer Membrane"; Eur. Polym. J. vol. 33 No. 7; pp. 1009-1014 (1997).

Consolvo, Sunny et al., "Design Requirement for Technologies that Encourage Physical Activity," CHI 2006 Proceedings, Designing for Tangible Interactions, Apr. 22, 2006, Montreal, Quebec, Canada, pp. 457-466.

Greene, "Medicaid Efforts to Incentivize Healthy Behaviours", Center for Health Care Strategies, Inc., Resource Paper, Jul. 2007.

Kendle, Earl R. And Morris, Larry A., "Preliminary Studies in the Development of a Gastric Battery for Fish" (1964). Nebraska Game and Parks Commission White Papers, Conference Presentations, & Manuscripts. Paper 22. pp. 1-6.

\* cited by examiner

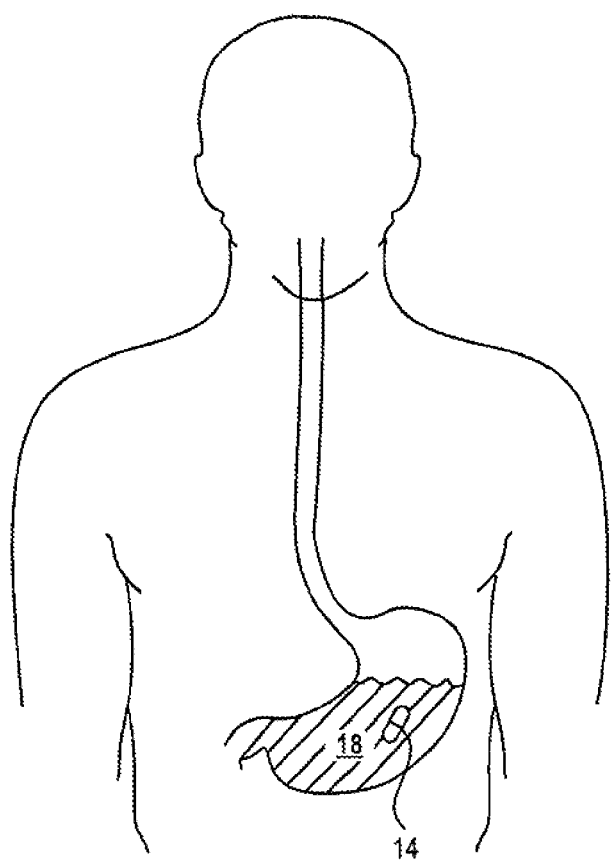
FIG. 1
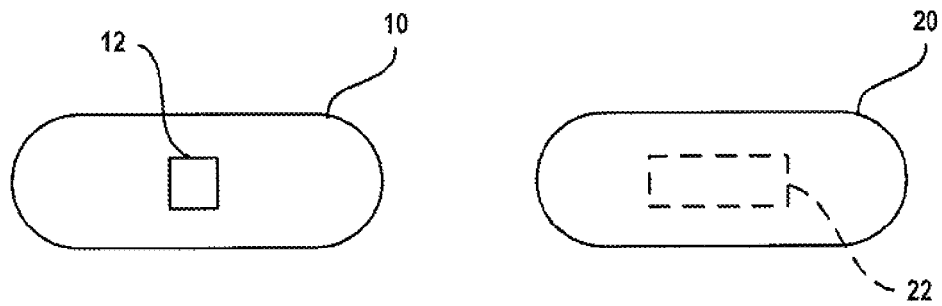
FIG. 2A     FIG. 2B

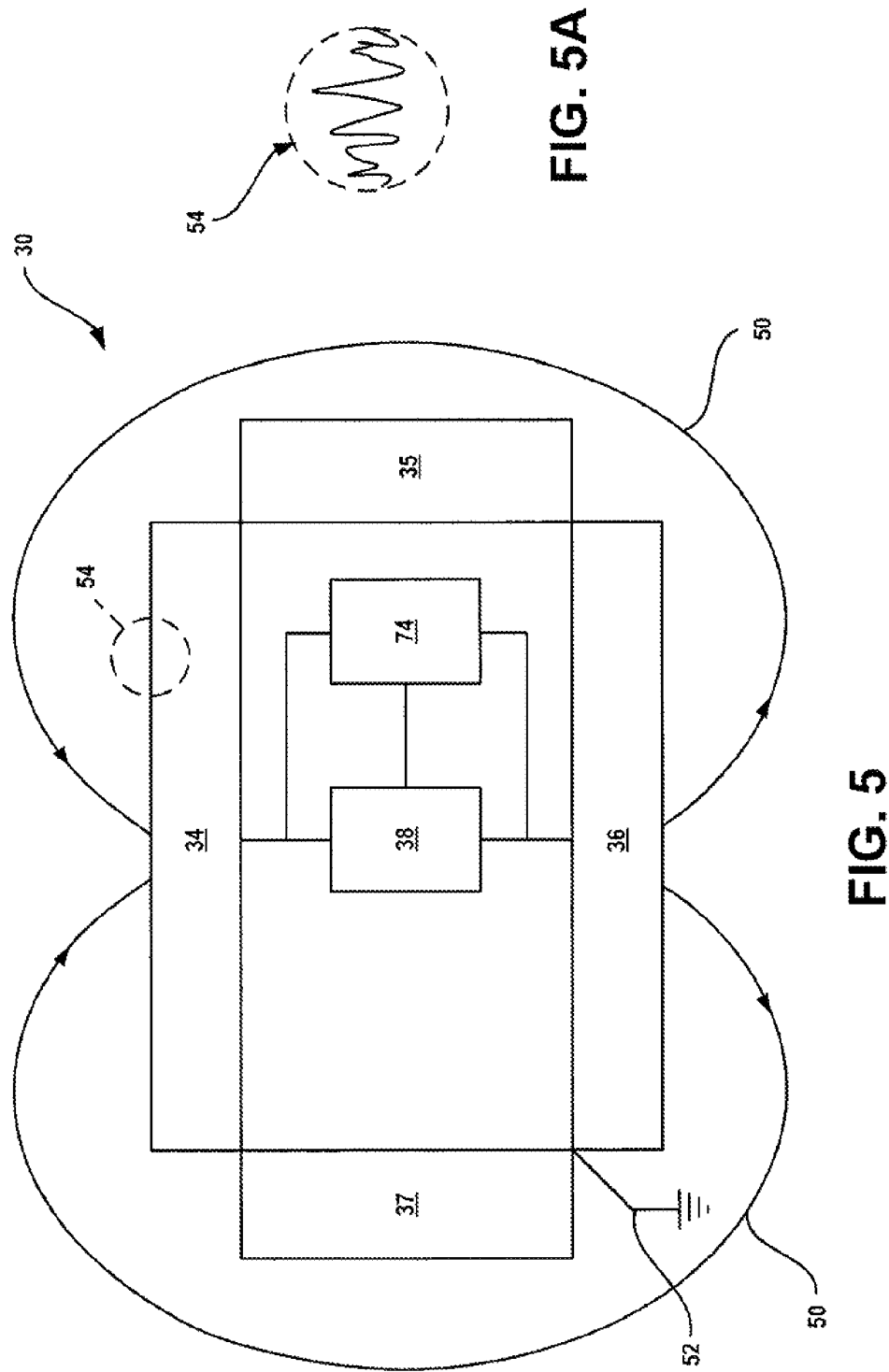

COMMUNICATION SYSTEM INCORPORATED IN A CONTAINER

CROSS-REFERENCE TO RELATED APPLICATIONS

This application is related to U.S. patent application Ser. No. 13/180,507 filed on Jul. 11, 2011 and entitled COMMUNICATION SYSTEM INCORPORATED IN AN INGESTIBLE PRODUCT, now U.S. Pat. No. 8,836,513 which is a continuation-in-part of U.S. Patent Application Publication 2010/0081894A1, now U.S. Pat. No. 7,978,064 and entitled COMMUNICATION SYSTEM WITH PARTIAL POWER SOURCE which is a continuation-in-part application of U.S. patent application Ser. No. 11/912,475 filed Jun. 23, 2008, now U.S. Pat. No. 8,847,766: which application is a 371 application of PCT Application Serial No. PCT/US06/16370 filed Apr. 28, 2006; which application pursuant to 35 U.S.C. §119 (e), claims priority to the filing dates of: U.S. Provisional Patent Application Ser. No. 60/676,145 filed Apr. 28, 2005; U.S. Provisional Patent Application Ser. No. 60/694,078 filed Jun. 24, 2005; U.S. Provisional Patent Application Ser. No. 60/713,680 filed Sep. 1, 2005 and U.S. Provisional Patent Application Ser. No. 60/790,335 filed Apr. 7, 2006; the disclosures of which are herein incorporated by reference.

This application is related to the following US Applications, the disclosures of which are incorporate herein by reference: U.S. application Ser. No. 13/180,516, filed Jul. 11, 2011 and entitled COMMUNICATION SYSTEM WITH REMOTE ACTIVATION, now U.S. Pat. No. 8,912,908; U.S. application Ser. No. 13/180,525 filed on Jul. 11, 2011 and entitled COMMUNICATION SYSTEM WITH ENHANCED PARTIAL POWER AND METHOD OF MANUFACTURING SAME, now U.S. Pat. No. 8,802,183; U.S. application Ser. No. 13/180,498, filed Jul. 11, 2011 and entitled COMMUNICATION SYSTEM WITH MULTIPLE TYPES OF POWER, now U.S. Patent Application Publication No. 2012/0004520; U.S. application Ser. No. 13/180,538, filed Jul. 11, 2011 and entitled COMMUNICATION SYSTEM USING POLYPHARMACY CO-PACKAGED MEDICATION DOSING UNIT, now U.S. Patent Application Publication No. 2012/0024889; U.S. application Ser. No. 13/180,539, filed Jul. 11, 2011 and entitled COMMUNICATION SYSTEM USING AN IMPLANTABLE DEVICE, now U.S. Pat. No. 8,730,031.

FIELD

The present invention is related to communication systems for detection of an event. More specifically, the present disclosure includes a system that includes a device for association with ingestible ingredients or products.

INTRODUCTION

Various devices and products are used for tracking food consumption. Examples of such devices or products have typically required human input or intervention in order to correlate the information associated with the type of food taken, the timing of consumption, and the amount of food consumed. Additionally, even if collection of some information is automated, human input is needed to match the information with the actual consumer so that there is a direct connection between the information and the person that consumed the food.

Given that there are so many different variables and types of information to track, the known systems do not provide an accurate means for tracking food consumption because of the need to rely upon human entry of data. Therefore, what is needed is a system and method for automating the tracking of food consumption, including timing of consumption, quantity of consumption, and identity of the consumer along with other information such as when a container is opened.

SUMMARY

The present disclosure includes a system for automation of the monitoring and tracking of consumption of food products. The system includes a container with a sensor that can communicate to a receiver. The container also includes sensors that measure the amount of food consumed and information related to the timing of the intent to consume as well as the timing of the consumption. The information can also be used to determine the identity of the consumer by using an ingestible device that produces a unique signature once inside the consumer's body.

BRIEF DESCRIPTION OF THE FIGURES

FIG. 1 shows an event indicator system in communication with an implanted device in according to the teaching of the present invention.

FIG. 2A shows the pharmaceutical product of FIG. 1 with the event indicator system on the exterior of the pharmaceutical product in accordance with the teachings of the present invention.

FIG. 2B shows the pharmaceutical product of FIG. 1 with the event indicator system positioned inside the pharmaceutical product in accordance with the teachings of the present invention.

FIG. 5 shows ionic transfer or the current path through a conducting fluid when the event indicator system of FIG. 3 is in contact with conducting liquid and in an active state in accordance with the teachings of the present invention.

FIG. 5A shows an exploded view of the surface of dissimilar materials of FIG. 5, in accordance with the teachings of the present invention.

DETAILED DESCRIPTION

Figure 3:
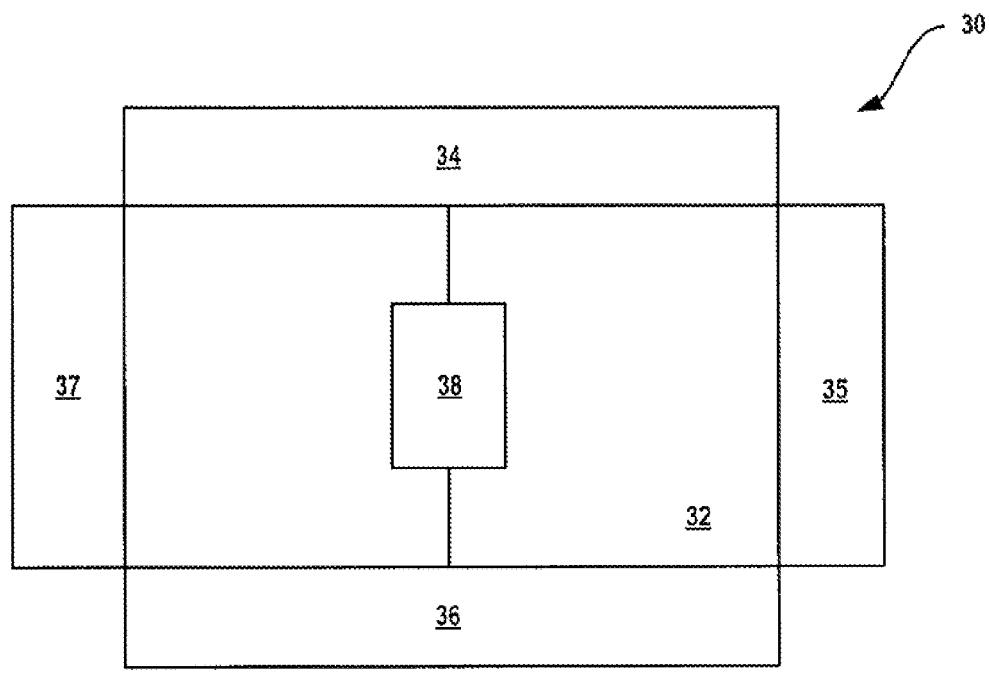
FIG. 3 is a block diagram representation of one aspect of the event indicator system with dissimilar metals positioned on opposite ends in accordance with the teachings of the present invention.

The present invention discloses an apparatus that is part of a system. The apparatus that includes a container and a sensor, as discussed in detail below. In accordance with one aspect of the present invention, the sensor is air activated. In accordance with another aspect of the present invention the sensor is activated upon contact with a conduction liquid or fluid, such as a drink or physiological fluid. The container can also measure the quantity food in the container and includes multiple aspects for indicating the occurrence of an event.

As described in more detail below, the system of the present invention is used with a conducting fluid to indicate the event marked by contact between the conducting fluid and the system. For example, the system of the present disclosure may be used with pharmaceutical product and the event that is indicated is when the product is taken or ingested. The term "ingested" or "ingest" or "ingesting" is understood to mean any introduction of the system internal to the body. For example, ingesting includes simply placing the system in the mouth all the way to the descending colon. Thus, the term ingesting refers to any instant in time when the system is introduced to an environment that contains a conducting fluid. Another example would be a situation when a non-conducting fluid is mixed with a conducting fluid. In such a situation the system would be present in the non-conduction fluid and when the two fluids are mixed, the system comes into contact with the conducting fluid and the system is activated. Yet another example would be the situation when the presence of certain conducting fluids needed to be detected. In such instances, the presence of the system, which would be activated, within the conducting fluid could be detected and, hence, the presence of the respective fluid would be detected.

Referring again to the instance where the system is used with the product that is ingested by the living organism, when the product that includes the system is taken or ingested, the device comes into contact with the conducting liquid of the body. When the system of the present invention comes into contact with the body fluid, a voltage potential is created and the system is activated. A portion of the power source is provided by the device, while another portion of the power source is provided by the conducting fluid, which is discussed in detail below.

Referring now to FIG. 1, an ingestible capsule 14 that includes a system of the present invention is shown inside the body. The capsule 14 is configured as an orally ingestible pharmaceutical formulation in the form of a pill or capsule. Upon ingestion, the capsule 14 moves to the stomach. Upon reaching the stomach, the capsule 14 is in contact with stomach fluid 18 and undergoes a chemical reaction with the various materials in the stomach fluid 18, such as hydrochloric acid and other digestive agents. The system of the present invention is discussed in reference to a pharmaceutical environment. However, the scope of the present invention is not limited thereby. The present invention can be used in any environment where a conducting fluid is present or becomes present through mixing of two or more components that result in a conducting liquid.

Referring now to FIG. 2A, a pharmaceutical product 10, similar to the capsule 14 of FIG. 1, is shown with a system 12, such as an ingestible event marker or an ionic emission module. The scope of the present invention is not limited by the shape or type of the product 10. For example, it will be clear to one skilled in the art that the product 10 can be a capsule, a time-release oral dosage, a tablet, a gel cap, a sub-lingual tablet, or any oral dosage product that can be combined with the system 12.

Additionally, the system 12 of the present invention may be ingested without a pharmaceutical product via a carrier capsule that includes only the system with no other active agent. In accordance with another aspect of the present invention, the system 12 may be used as part of a food product or an ingredient in a food product. For example, the system 12 is coated with a protective material as discussed in detail below. The system 12 is then included is the food product similar to any ingredient. Thus, ingestion of that food product may be tracked automatically, which is often useful in setting where knowing the exact food take and time of ingestion is needed, for example when a person has a special diet or is receiving care at a hospital as a patient or in-patient.

In accordance with another example of the present invention, the system 12 may be combined with an ingredient commonly used in making food. For example, the system 12 may be secured to salt in a manner similar to the way the system 12 is secured to a pharmaceutical product, as discussed below. Then as the ingredient with the system 12 is mixed into the food, the food will include the system which will become activated upon ingestion.

In accordance with various aspects of the present invention, when the system 12 is combined with food and ingested there are various approaches to activation of the system 12. In accordance with one aspect of the present invention, the system 12 may be coated with a material that breaks and releases the system 12 as the food is being masticated, e.g. chewed or squashed. In accordance with another aspect of the present invention, the coating material may be reactive to saliva and when in contact with saliva will dissolve or disintegrate and release the system 12. Conducting fluids associated with saliva may activate the system 12. In accordance with yet another aspect of the present invention, the coating material may be reactive to stomach acids and dissolve or disintegrate upon contact with the stomach fluids to release the system 12. In accordance with another aspect of the present invention, the coating material may be made of material that resists breaking or dissolving when masticated or exposed to saliva, such as the beads found in drinks. In accordance with another aspect of the present invention, the coating material may be intentionally destroyed or broken apart when distributed or mixed in with a food, such as when bread is mixed and prepared for a food (e.g. pizza dough).

Continuing with FIG. 2A, in the shown aspect, the product 10 has the system 12 secured to the exterior using known methods of securing micro-devices to the exterior of pharmaceutical products or an ingestible ingredient, for example food or ingredients of food. Example of methods for securing the micro-device to the product is disclosed in U.S. Provisional Application No. 61/142,849 filed on Jan. 1, 2009 and entitled "HIGH-THROUGHPUT PRODUCTION OF INGESTIBLE EVENT MARKERS" as well as U.S. Provisional Application No. 61/177,611 filed on May 12, 2009 and entitled "INGESTIBLE EVENT MARKERS COMPRISING AN IDENTIFIER AND AN INGESTIBLE COMPONENT", the entire disclosure of each is incorporated herein by reference. Once ingested, the system 12 comes into contact with body liquids and the system 12 is activated. The system 12 uses the voltage potential difference to power up and thereafter modulates conductance to create a unique and identifiable current signature. Upon activation, the system 12 controls the conductance and, hence, current flow to produce the current signature.

There are various reasons for delaying the activation of the system 12. In order to delay the activation of the system 12, the system 12 may be coated with a shielding material or protective layer. The layer is dissolved over a period of time, thereby allowing the system 12 to be activated when the product 10 has reached a target location.

Referring now to FIG. 2B, a pharmaceutical product or an ingestible product/ingredient 20, similar to the capsule 14 of FIG. 1, is shown with a system 22, such as an ingestible event marker or an identifiable emission module. The scope of the present invention is not limited by the environment to which the system 22 is introduced. For example, the system 22 can be enclosed in a capsule that is taken in addition to/independently from the pharmaceutical product or ingestible ingredient. The capsule may be simply a carrier for the system 22 and may not contain any product. Furthermore, the scope of the present invention is not limited by the shape or type of product 20. For example, it will be clear to one skilled in the art that the product 20 can be a food product or ingredient, a capsule, a time-release oral dosage, a tablet, a gel capsule, a sub-lingual tablet, or any oral dosage product. In the referenced aspect, the product 20 has the system 22 positioned inside or secured to the interior of the product 20. In one aspect, the system 22 is secured to the interior wall of the product 20. When the system 22 is positioned inside a gel capsule, then the content of the gel capsule is a non-conducting gel-liquid. On the other hand, if the content of the gel capsule is a conducting gel-liquid, then in an alternative aspect, the system 22 is coated with a protective cover to prevent unwanted activation by the gel capsule content. If the content of the capsule is a dry powder or microspheres, then the system 22 is positioned or placed within the capsule. If the product 20 is a tablet or hard pill, then the system 22 is held in place inside the tablet. Once ingested, the product 20 containing the system 22 is dissolved. The system 22 comes into contact with body liquids and the system 22 is activated. Depending on the product 20, the system 22 may be positioned in either a near-central or near-perimeter position depending on the desired activation delay between the time of initial ingestion and activation of the system 22. For example, a central position for the system 22 means that it will take longer for the system 22 to be in contact with the conducting liquid and, hence, it will take longer for the system 22 to be activated. Therefore, it will take longer for the occurrence of the event to be detected.

Referring now to FIG. 3, in one aspect, the systems 12 and 22 of FIGS. 2A and 2B, respectively, are shown in more detail as system 30. The system 30 can be used in association with any pharmaceutical product, as mentioned above, to determine when a patient takes the pharmaceutical product. As indicated above, the scope of the present invention is not limited by the environment and the product that is used with the system 30. For example, the system 30 may be placed within a capsule and the capsule is placed within the conducting liquid. The capsule would then dissolve over a period of time and release the system 30 into the conducting liquid. Thus, in one aspect, the capsule would contain the system 30 and no product. Such a capsule may then be used in any environment where a conducting liquid is present and with any product. For example, the capsule may be dropped into a container filled with jet fuel, salt water, tomato sauce, motor oil, or any similar product. Additionally, the capsule containing the system 30 may be ingested at the same time that any pharmaceutical product is ingested in order to record the occurrence of the event, such as when the product was taken.

In the specific example of the system 30 combined with the pharmaceutical product, as the product or pill is ingested, the system 30 is activated. The system 30 controls conductance to produce a unique current signature that is detected, thereby signifying that the pharmaceutical product has been taken. The system 30 includes a framework 32. The framework 32 is a chassis for the system 30 and multiple components are attached to, deposited upon, or secured to the framework 32. In this aspect of the system 30, a digestible material 34 is physically associated with the framework 32. The material 34 may be chemically deposited on, evaporated onto, secured to, or built-up on the framework all of which may be referred to herein as "deposit" with respect to the framework 32. The material 34 is deposited on one side of the framework 32. The materials of interest that can be used as material 34 include, but are not limited to: Cu or CuI. The material 34 is deposited by physical vapor deposition, electrodeposition, or plasma deposition, among other protocols. The material 34 may be from about 0.05 to about 500 µm thick, such as from about 5 to about 100 µm thick. The shape is controlled by shadow mask deposition, or photolithography and etching. Additionally, even though only one region is shown for depositing the material, each system 30 may contain two or more electrically unique regions where the material 34 may be deposited, as desired.

At a different side, which is the opposite side as shown in FIG. 3, another digestible material 36 is deposited, such that materials 34 and 36 are dissimilar. Although not shown, the different side selected may be the side next to the side selected for the material 34. The scope of the present invention is not limited by the side selected and the term "different side" can mean any of the multiple sides that are different from the first selected side. Furthermore, even though the shape of the system is shown as a square, the shape may be any geometrically suitable shape. Material 34 and 36 are selected such that they produce a voltage potential difference when the system 30 is in contact with conducting liquid, such as body fluids. The materials of interest for material 36 include, but are not limited to: Mg, Zn, or other electronegative metals. As indicated above with respect to the material 34, the material 36 may be chemically deposited on, evaporated onto, secured to, or built-up on the framework. Also, an adhesion layer may be necessary to help the material 36 (as well as material 34 when needed) to adhere to the framework 32. Typical adhesion layers for the material 36 are Ti, TiW, Cr or similar material. Anode material and the adhesion layer may be deposited by physical vapor deposition, electrodeposition or plasma deposition. The material 36 may be from about 0.05 to about 500 µm thick, such as from about 5 to about 100 µm thick. However, the scope of the present invention is not limited by the thickness of any of the materials nor by the type of process used to deposit or secure the materials to the framework 32.

According to the disclosure set forth, the materials 34 and 36 can be any pair of materials with different electrochemical potentials. Additionally, in the aspects wherein the system 30 is used in-vivo, the materials 34 and 36 may be vitamins that can be absorbed. More specifically, the materials 34 and 36 can be made of any two materials appropriate for the environment in which the system 30 will be operating. For example, when used with an ingestible product, the materials 34 and 36 are any pair of materials with different electrochemical potentials that are ingestible. An illustrative example includes the instance when the system 30 is in contact with an ionic solution, such as stomach acids. Suitable materials are not restricted to metals, and in certain aspects the paired materials are chosen from metals and non-metals, e.g., a pair made up of a metal (such as Mg) and a salt (such as CuCl or CuI). With respect to the active electrode materials, any pairing of substances—metals, salts, or intercalation compounds—with suitably different electrochemical potentials (voltage) and low interfacial resistance are suitable.

Materials and pairings of interest include, but are not limited to, those reported in Table 1 below. In one aspect, one or both of the metals may be doped with a non-metal, e.g., to enhance the voltage potential created between the materials as they come into contact with a conducting liquid. Non-metals that may be used as doping agents in certain aspects include, but are not limited to: sulfur, iodine and the like. In another aspect, the materials are copper iodine (CuI) as the anode and magnesium (Mg) as the cathode. Aspects of the present invention use electrode materials that are not harmful to the human body.

TABLE 1

|  | Anode | Cathode |
|---|---|---|
| Metals | Magnesium, Zinc Sodium, Lithium Iron | |
| Salts | | Copper salts: iodide, chloride, bromide, sulfate, formate, (other anions possible) $Fe^{3+}$ salts: e.g. orthophosphate, pyrophosphate, (other anions possible) Oxygen on platinum, gold or other catalytic surfaces |
| Intercalation compounds | Graphite with Li, K, Ca, Na, Mg | Vanadium oxide Manganese oxide |

Thus, when the system 30 is in contact with the conducting liquid, a current path, an example is shown in FIG. 5, is formed through the conducting liquid between material 34 and 36. A control device 38 is secured to the framework 32 and electrically coupled to the materials 34 and 36. The control device 38 includes electronic circuitry, for example control logic that is capable of controlling and altering the conductance between the materials 34 and 36.

The voltage potential created between the materials 34 and 36 provides the power for operating the system as well as produces the current flow through the conducting fluid and the system. In one aspect, the system operates in direct current mode. In an alternative aspect, the system controls the direction of the current so that the direction of current is reversed in a cyclic manner, similar to alternating current. As the system reaches the conducting fluid or the electrolyte, where the fluid or electrolyte component is provided by a physiological fluid, e.g., stomach acid, the path for current flow between the materials 34 and 36 is completed external to the system 30; the current path through the system 30 is controlled by the control device 38. Completion of the current path allows for the current to flow and in turn a receiver, not shown, can detect the presence of the current and recognize that the system 30 has been activate and the desired event is occurring or has occurred.

In one aspect, the two materials 34 and 36 are similar in function to the two electrodes needed for a direct current power source, such as a battery. The conducting liquid acts as the electrolyte needed to complete the power source. The completed power source described is defined by the physical chemical reaction between the materials 34 and 36 of the system 30 and the surrounding fluids of the body. The completed power source may be viewed as a power source that exploits reverse electrolysis in an ionic or a conducting solution such as gastric fluid, blood, or other bodily fluids and some tissues. Additionally, the environment may be something other than a body and the liquid may be any conducting liquid. For example, the conducting fluid may be salt water or a metallic based paint.

In certain aspects, these two materials are shielded from the surrounding environment by an additional layer of material. Accordingly, when the shield is dissolved and the two dissimilar materials are exposed to the target site, a voltage potential is generated.

In certain aspects, the complete power source or supply is one that is made up of active electrode materials, electrolytes, and inactive materials, such as current collectors, packaging, etc. The active materials are any pair of materials with different electrochemical potentials. Suitable materials are not restricted to metals, and in certain aspects the paired materials are chosen from metals and non-metals, e.g., a pair made up of a metal (such as Mg) and a salt (such as CuI). With respect to the active electrode materials, any pairing of substances—metals, salts, or intercalation compounds—with suitably different electrochemical potentials (voltage) and low interfacial resistance are suitable.

A variety of different materials may be employed as the materials that form the electrodes. In certain aspects, electrode materials are chosen to provide for a voltage upon contact with the target physiological site, e.g., the stomach, sufficient to drive the system of the identifier. In certain aspects, the voltage provided by the electrode materials upon contact of the metals of the power source with the target physiological site is 0.001 V or higher, including 0.01 V or higher, such as 0.1 V or higher, e.g., 0.3 V or higher, including 0.5 volts or higher, and including 1.0 volts or higher, where in certain aspects, the voltage ranges from about 0.001 to about 10 volts, such as from about 0.01 to about 10 V.

Referring again to FIG. 3, the materials 34 and 36 provide the voltage potential to activate the control device 38. Once the control device 38 is activated or powered up, the control device 38 can alter conductance between the materials 34 and 36 in a unique manner. By altering the conductance between materials 34 and 36, the control device 38 is capable of controlling the magnitude of the current through the conducting liquid that surrounds the system 30. This produces a unique current signature that can be detected and measured by a receiver (not shown), which can be positioned internal or external to the body. In addition to controlling the magnitude of the current path between the materials, non-conducting materials, membrane, or "skirt" are used to increase the "length" of the current path and, hence, act to boost the conductance path, as disclosed in the U.S. patent application Ser. No. 12/238,345 entitled, "In-Body Device with Virtual Dipole Signal Amplification" filed Sep. 25, 2008, the entire content of which is incorporated herein by reference. Alternatively, throughout the disclosure herein, the terms "non-conducting material", "membrane", and "skirt" are interchangeably with the term "current path extender" without impacting the scope or the present aspects and the claims herein. The skirt, shown in portion at 35 and 37, respectively, may be associated with, e.g., secured to, the framework 32. Various shapes and configurations for the skirt are contemplated as within the scope of the present invention. For example, the system 30 may be surrounded entirely or partially by the skirt and the skirt maybe positioned along a central axis of the system 30 or off-center relative to a central axis. Thus, the scope of the present invention as claimed herein is not limited by the shape or size of the skirt. Furthermore, in other aspects, the materials 34 and 36 may be separated by one skirt that is positioned in any defined region between the materials 34 and 36.

Figure 4:
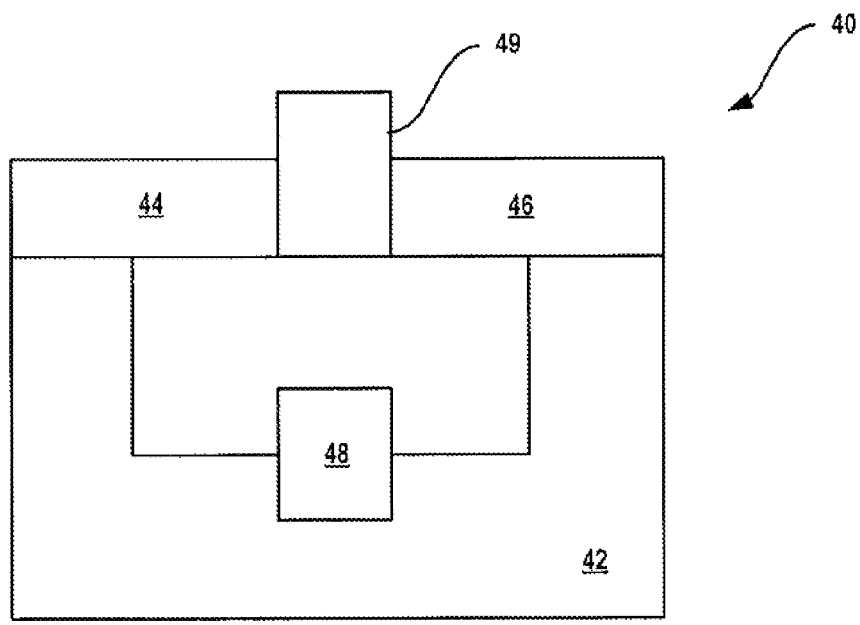
FIG. 4 is a block diagram representation of another aspect of the event indicator system with dissimilar metals positioned on the same end and separated by a non-conducting material in accordance with the teachings of the present invention.

Referring now to FIG. 4, in another aspect, the systems 12 and 22 of FIGS. 2A and 2B, respectively, are shown in more detail as system 40. The system 40 includes a framework 42. The framework 42 is similar to the framework 32 of FIG. 3. In this aspect of the system 40, a digestible or dissolvable material 44 is deposited on a portion of one side of the framework 42. At a different portion of the same side of the framework 42, another digestible material 46 is deposited, such that materials 44 and 46 are dissimilar. More specifically, material 44 and 46 are selected such that they form a voltage potential difference when in contact with a conducting liquid, such as body fluids. Thus, when the system 40 is in contact with and/or partially in contact with the conducting liquid, then a current path, an example is shown in FIG. 5, is formed through the conducting liquid between material 44 and 46. A control device 48 is secured to the framework 42 and electrically coupled to the materials 44 and 46. The control device 48 includes electronic circuitry that is capable of controlling part of the conductance path between the materials 44 and 46. The materials 44 and 46 are separated by a non-conducting skirt 49. Various examples of the skirt 49 are disclosed in U.S. Provisional Application No. 61/173,511 filed on Apr. 28, 2009 and entitled "HIGHLY RELIABLE INGESTIBLE EVENT MARKERS AND METHODS OF USING SAME" and U.S. Provisional Application No. 61/173,564 filed on Apr. 28, 2009 and entitled "INGESTIBLE EVENT MARKERS HAVING SIGNAL AMPLIFIERS THAT COMPRISE AN ACTIVE AGENT"; as well as U.S. application Ser. No. 12/238,345 filed Sep. 25, 2008 and entitled "IN-BODY DEVICE WITH VIRTUAL DIPOLE SIGNAL AMPLIFICATION"; the entire disclosure of each is incorporated herein by reference.

Once the control device 48 is activated or powered up, the control device 48 can alter conductance between the materials 44 and 46. Thus, the control device 48 is capable of controlling the magnitude of the current through the conducting liquid that surrounds the system 40. As indicated above with respect to system 30, a unique current signature that is associated with the system 40 can be detected by a receiver (not shown) to mark the activation of the system 40. In order to increase the "length" of the current path the size of the skirt 49 is altered. The longer the current path, the easier it may be for the receiver to detect the current.

Referring now to FIG. 5, the system 30 of FIG. 3 is shown in an activated state and in contact with conducting liquid. The system 30 is grounded through ground contact 52. For example, when the system 30 is in contact with a conducting fluid, the conducting fluid provides the ground. The system 30 also includes a sensor module 74, which is described in greater detail with respect to FIG. 6. Ion or current paths 50 between material 34 to material 36 and through the conducting fluid in contact with the system 30. The voltage potential created between the material 34 and 36 is created through chemical reactions between materials 34/36 and the conducting fluid.

The system 30 also includes a unit 75. The unit 75 includes communication functions and in accordance with the various aspects of the present invention can act as any of the following: a receiver, a transmitter, or a transceiver. Thus, another device that is external to the system 30, such as a cell phone, an implanted device, a device attached to the user's body, or a device placed under the user's skin can communicate with the system 30 through the unit 75. The unit 75 is also electrically connected to the materials 34 and 36. In accordance with one aspect of the present invention, any device that is external to the system 30 may communicate with either the unit 75 or the control module 38 using current flow through the environment surrounding the system 30. For example, a patch or receiver that is attached to the user's body, a cell phone or device being held by the user, or an implanted device, any of which can generate a current signature through the user's body. The current signature can include information that is encoded therein. The current signature is detected by the system 30, using the unit 75 or the control module 38, and decoded to allow communication to the system 30 from the device external to system 30. Accordingly, the external device can send a signal to the unit 75, either wirelessly or through transconduction, that controls the activation of the system 30.

Referring now to FIG. 5A shows an exploded view of the surface of the material 34. The surface of the material 34 is not planar, but rather an irregular surface. The irregular surface increases the surface area of the material and, hence, the area that comes in contact with the conducting fluid. In one aspect, at the surface of the material 34, there is an electrochemical reaction between the material 34 and the surrounding conducting fluid such that mass is released into the conducting fluid. The term "mass" as used herein refers to protons and neutrons that form a substance. One example includes the instant where the material is CuCl and when in contact with the conducting fluid, CuCl becomes Cu (solid) and Cl⁻ in solution. The flow of positive ions into the conducting fluid is depicted by the current path 50. Negative ions flow in the opposite direction. In a similar manner, there is an electrochemical reaction between the material 36 and the surrounding conducting fluid. In this example, the release of negative ions at the material 34 and release of positive ion by the material 36 is collectively referred to as the ionic exchange. The rate of ionic exchange and, hence the ionic emission rate or flow, is controlled by the control device 38. The control device 38 can increase or decrease the rate of ion flow by altering the conductance, which alters the impedance, between the materials 34 and 36. Through controlling the ion exchange, the system 30 can encode information in the ionic exchange process. Thus, the system 30 uses ionic emission to encode information in the ionic exchange.

The control device 38 can vary the duration of a fixed ionic exchange rate or current flow magnitude while keeping the rate or magnitude near constant, similar to when the frequency is modulated and the amplitude is constant. Also, the control device 38 can vary the level of the ionic exchange rate or the magnitude of the current flow while keeping the duration near constant. Thus, using various combinations of changes in duration and altering the rate or magnitude, the control device 38 encodes information in the current flow or the ionic exchange. For example, the control device 38 may use, but is not limited to any of the following techniques namely, Binary Phase-Shift Keying (PSK), Frequency modulation, Amplitude modulation, on-off keying, and PSK with on-off keying.

As indicated above, the various aspects disclosed herein, such as systems 30 and 40 of FIGS. 3 and 4, respectively, include electronic components as part of the control device 38 or the control device 48. Components that may be present include but are not limited to: logic and/or memory elements, an integrated circuit, an inductor, a resistor, and sensors for measuring various parameters. Each component may be secured to the framework and/or to another component. The components on the surface of the support may be laid out in any convenient configuration. Where two or more components are present on the surface of the solid support, interconnects may be provided.

As indicated above, the system, such as system 30 and 40, control the conductance between the dissimilar materials and, hence, the rate of ionic exchange or the current flow. Through altering the conductance in a specific manner the system is capable of encoding information in the ionic exchange and the current signature. The ionic exchange or the current signature is used to uniquely identify the specific system. Additionally, the systems 30 and 40 are capable of producing various different unique exchanges or signatures and, thus, provide additional information. For example, a second current signature based on a second conductance alteration pattern may be used to provide additional information, which information may be related to the physical environment. To further illustrate, a first current signature may be a very low current state that maintains an oscillator on the chip and a second current signature may be a current state at least a factor of ten higher than the current state associated with the first current signature.

Figure 5B:
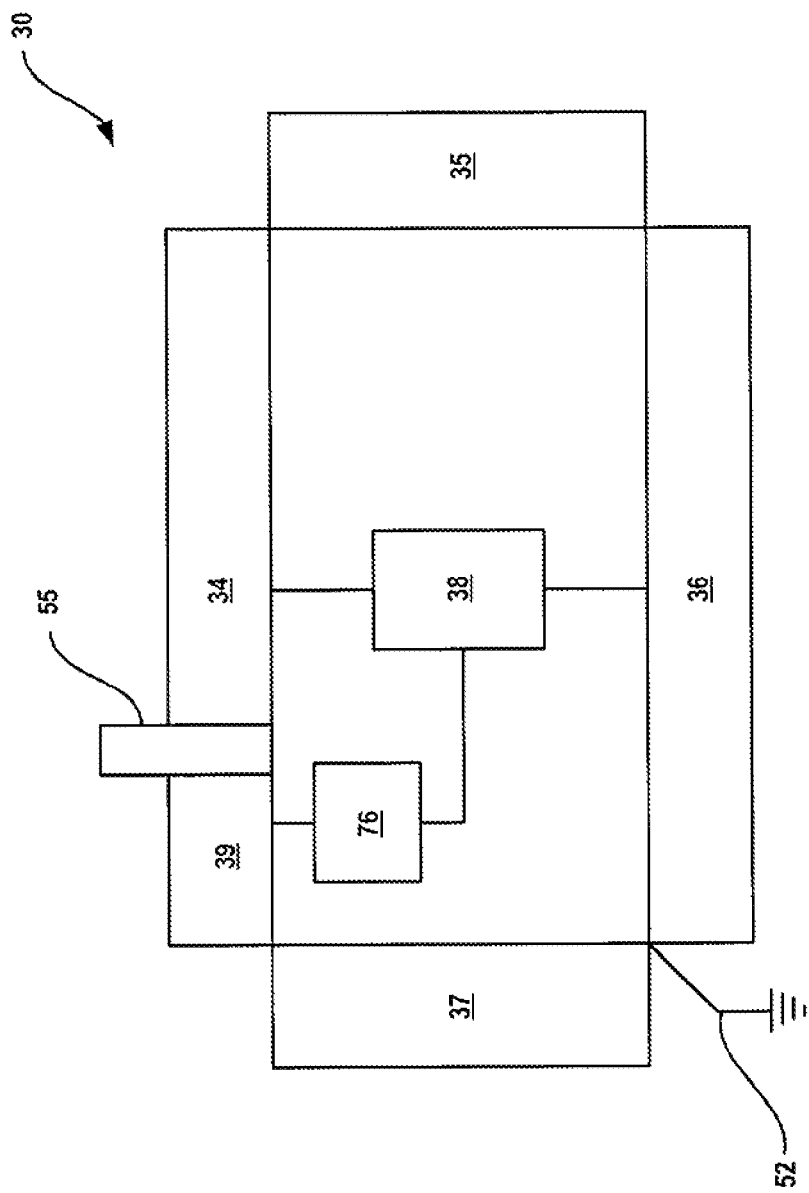
FIG. 5B shows the event indicator system of FIG. 5 with a pH sensor unit, in accordance with the teachings of the present invention.
Figure 6:
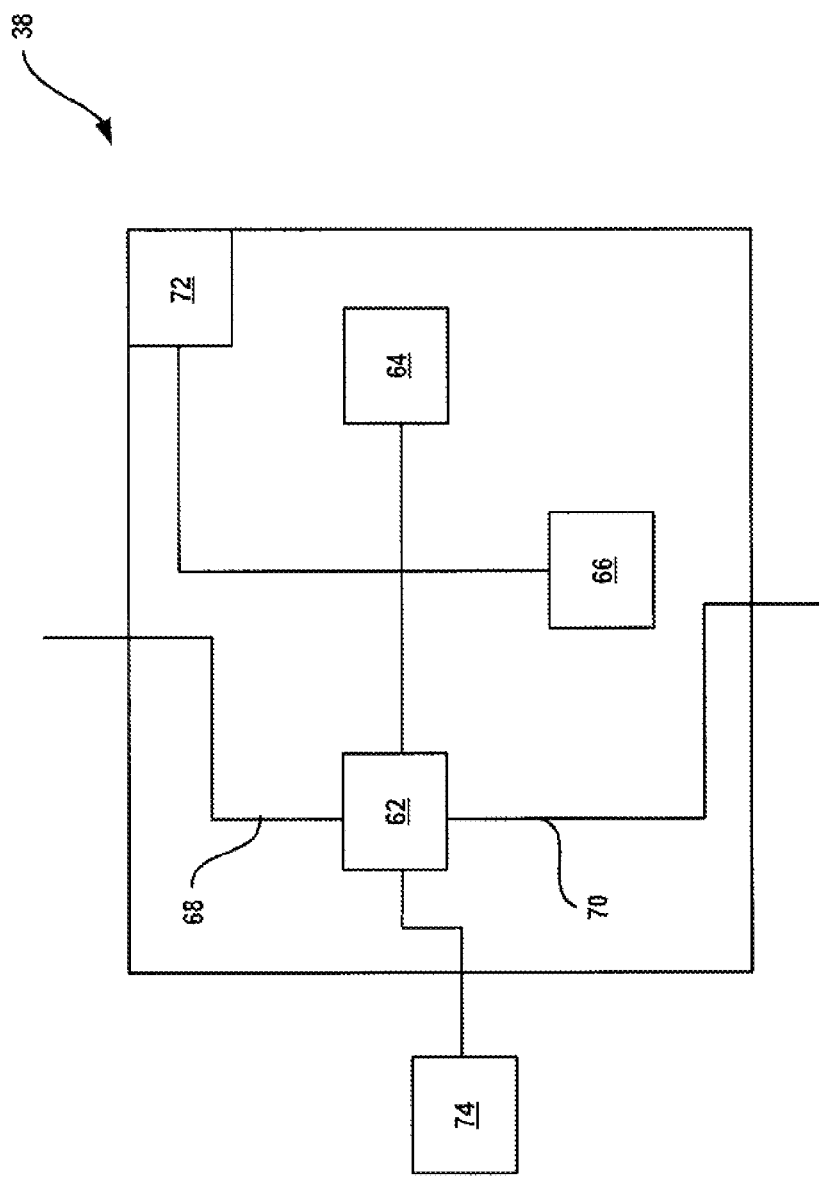
FIG. 6 is a block diagram illustration of one aspect of the control device used in the system of FIGS. 3 and 4, in accordance with the teachings of the present invention.

Referring now to FIG. 6, a block diagram representation of the control device 38 is shown. The control device 30 includes a control module 62, a counter or clock 64, and a memory 66. Additionally, the device 38 is shown to include a sensor module 72 as well as the sensor module 74, which was referenced in FIG. 5. The control module 62 has an input 68 electrically coupled to the material 34 and an output 70 electrically coupled to the material 36. The control module 62, the clock 64, the memory 66, and the sensor modules 72/74 also have power inputs (some not shown). The power for each of these components is supplied by the voltage potential produced by the chemical reaction between materials 34 and 36 and the conducting fluid, when the system 30 is in contact with the conducting fluid. The control module 62 controls the conductance through logic that alters the overall impedance of the system 30. The control module 62 is electrically coupled to the clock 64. The clock 64 provides a clock cycle to the control module 62. Based upon the programmed characteristics of the control module 62, when a set number of clock cycles have passed, the control module 62 alters the conductance characteristics between materials 34 and 36. This cycle is repeated and thereby the control device 38 produces a unique current signature characteristic. The control module 62 is also electrically coupled to the memory 66. Both the clock 64 and the memory 66 are powered by the voltage potential created between the materials 34 and 36.

The control module 62 is also electrically coupled to and in communication with the sensor modules 72 and 74. In the aspect shown, the sensor module 72 is part of the control device 38 and the sensor module 74 is a separate component. In alternative aspects, either one of the sensor modules 72 and 74 can be used without the other and the scope of the present invention is not limited by the structural or functional location of the sensor modules 72 or 74. Additionally, any component of the system 30 may be functionally or structurally moved, combined, or repositioned without limiting the scope of the present invention as claimed. Thus, it is possible to have one single structure, for example a processor, which is designed to perform the functions of all of the following modules: the control module 62, the clock 64, the memory 66, and the sensor module 72 or 74. On the other hand, it is also within the scope of the present invention to have each of these functional components located in independent structures that are linked electrically and able to communicate.

Referring again to FIG. 6, the sensor modules 72 or 74 can include any of the following sensors: temperature, pressure, pH level, and conductivity. In one aspect, the sensor modules 72 or 74 gather information from the environment and communicate the analog information to the control module 62. The control module then converts the analog information to digital information and the digital information is encoded in the current flow or the rate of the transfer of mass that produces the ionic flow. In another aspect, the sensor modules 72 or 74 gather information from the environment and convert the analog information to digital information and then communicate the digital information to control module 62. In the aspect shown in FIG. 5, the sensor modules 74 is shown as being electrically coupled to the material 34 and 36 as well as the control device 38. In another aspect, as shown in FIG. 6, the sensor module 74 is electrically coupled to the control device 38 at connection 78. The connection 78 acts as both a source for power supply to the sensor module 74 and a communication channel between the sensor module 74 and the control device 38.

Referring now to FIG. 5B, the system 30 includes a pH sensor module 76 connected to a material 39, which is selected in accordance with the specific type of sensing function being performed. The pH sensor module 76 is also connected to the control device 38. The material 39 is electrically isolated from the material 34 by a non-conductive barrier 55. In one aspect, the material 39 is platinum. In operation, the pH sensor module 76 uses the voltage potential difference between the materials 34/36. The pH sensor module 76 measures the voltage potential difference between the material 34 and the material 39 and records that value for later comparison. The pH sensor module 76 also measures the voltage potential difference between the material 39 and the material 36 and records that value for later comparison. The pH sensor module 76 calculates the pH level of the surrounding environment using the voltage potential values. The pH sensor module 76 provides that information to the control device 38. The control device 38 varies the rate of the transfer of mass that produces the ionic transfer and the current flow to encode the information relevant to the pH level in the ionic transfer, which can be detected by a receiver (not shown). Thus, the system 30 can determine and provide the information related to the pH level to a source external to the environment.

As indicated above, the control device 38 can be programmed in advance to output a pre-defined current signature. In another aspect, the system can include a receiver system that can receive programming information when the system is activated. In another aspect, not shown, the switch 64 and the memory 66 can be combined into one device.

In addition to the above components, the system 30 may also include one or other electronic components. Electrical components of interest include, but are not limited to: additional logic and/or memory elements, e.g., in the form of an integrated circuit; a power regulation device, e.g., battery, fuel cell or capacitor; a sensor, a stimulator, etc.; a signal transmission element, e.g., in the form of an antenna, electrode, coil, etc.; a passive element, e.g., an inductor, resistor, etc.

In certain aspects, the ingestible circuitry includes a coating layer. The purpose of this coating layer can vary, e.g., to protect the circuitry, the chip and/or the battery, or any components during processing, during storage, or even during ingestion. In such instances, a coating on top of the circuitry may be included. Also of interest are coatings that are designed to protect the ingestible circuitry during storage, but dissolve immediately during use. For example, coatings that dissolve upon contact with an aqueous fluid, e.g. stomach fluid, or the conducting fluid as referenced above. Also of interest are protective processing coatings that are employed to allow the use of processing steps that would otherwise damage certain components of the device. For example, in aspects where a chip with dissimilar material deposited on the top and bottom is produced, the product needs to be diced. However, the dicing process can scratch off the dissimilar material, and also there might be liquid involved which would cause the dissimilar materials to discharge or dissolve. In such instances, a protective coating on the materials prevents mechanical or liquid contact with the component during processing can be employed. Another purpose of the dissolvable coatings may be to delay activation of the device. For example, the coating that sits on the dissimilar material and takes a certain period of time, e.g., five minutes, to dissolve upon contact with stomach fluid may be employed. The coating can also be an environmentally sensitive coating, e.g., a temperature or pH sensitive coating, or other chemically sensitive coating that provides for dissolution in a controlled fashion and allows one to activate the device when desired. Coatings that survive the stomach but dissolve in the intestine are also of interest, e.g., where one desires to delay activation until the device leaves the stomach. An example of such a coating is a polymer that is insoluble at low pH, but becomes soluble at a higher pH. Also of interest are pharmaceutical formulation protective coatings, e.g., a gel cap liquid protective coating that prevents the circuit from being activated by liquid of the gel cap.

Figure 7:
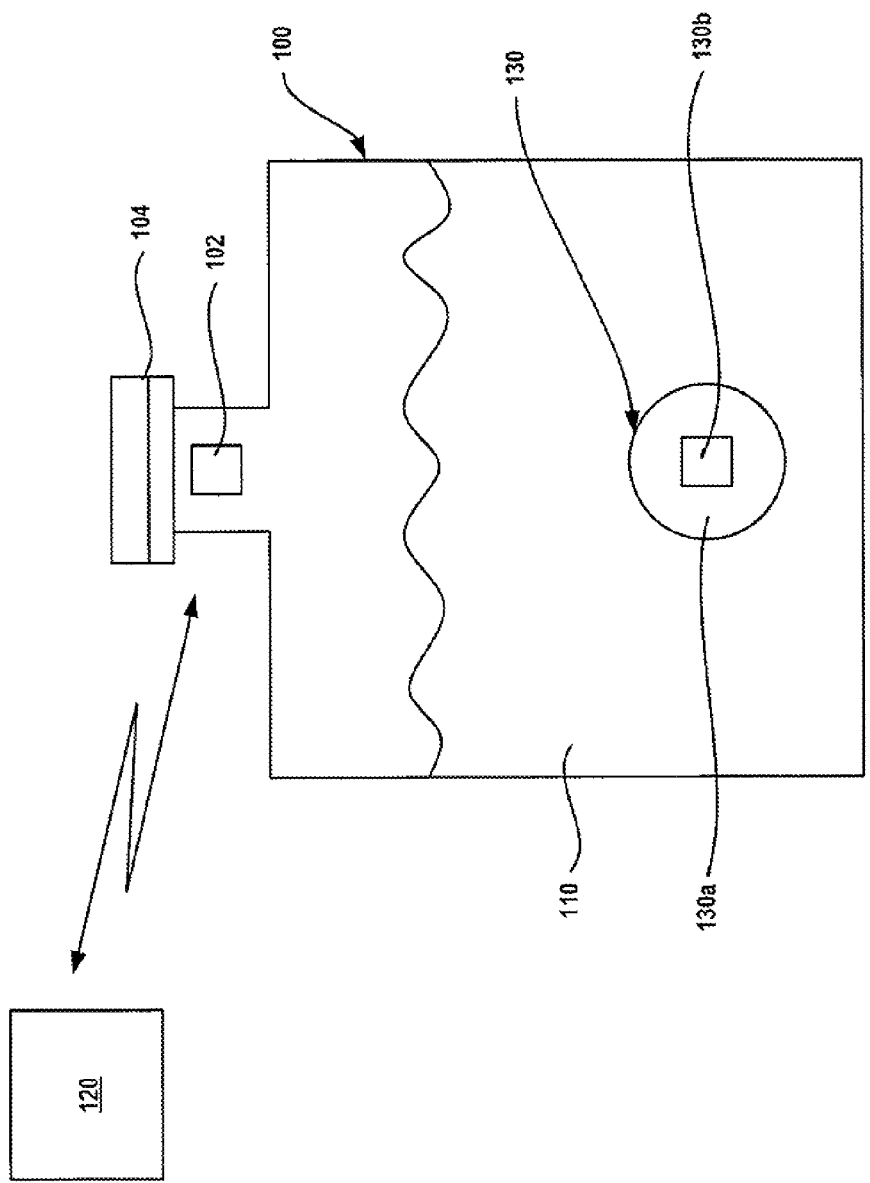
FIG. 7 shows a container for liquids with an event indicator in accordance with the teachings of the present invention.

Referring now to FIG. 7, a container 100 is shown that includes an event indicator 102. The container 100 holds liquid 110 that can be consumed by a consumer. The scope of the present invention is not limited by the type of consumable liquid within container 100. In accordance with one aspect of the present invention, the indicator 102 is placed at or near the opening of the container 100, such that as the liquid 110 is poured and comes into contact with the event indicator 102, the presence of the liquid 110 activates the indicator 102. As long as the liquid 110 is in contact with the indicator 102, such as while the liquid 100 is being poured, the indicator 102 remains active. Once activated, the indicator 102 communicates with a detector or receiver device 120. Thus, the device 120 can record the timing of the activation of the indicator 102.

In accordance with another aspect of the present invention, the indicator 102 can be activated by coming into contact with the consumer's mouth and is activated upon contact with the physiological fluids of the consumer, such as saliva. Once activated the indicator 102 communicates with the device 120, which may be positioned on or secured to the consumer's body or skin or part of the clothing worn by the consumer that is in contact with the consumer's skin. Thus, the device 120 could communicate with the indicator 102 through the consumer's body using transconduction or wirelessly through the air.

In accordance with other aspects of the present invention, additional indicators, such as an ingestible indicator 130 that includes a coating material 130a and a unit 130b, is present or included in the liquid 110. In accordance with one aspects of the present invention, the indicator 130 is similar to the indicator 102. Based on the various aspects of the present invention, the indicator 130 may be different from the indicator 102. In accordance with one aspects of the present invention, the coating 130a of the indicator 130 is designed to react with physiological fluids, such as stomach acids, and dissolve. Once the coating 130a is dissolved inside the consumer's body, the indicator 130 is activated and communicates with the device 120 using transconduction as indicated above. The scope of the present invention is not limited by the number of indicators 130 that are included in the liquid 110.

In accordance with another aspect of the present invention, the indicator 102 includes a zinc-air activated type battery. Thus, as a cap 104 is secured onto the container, the cap 104 isolates the indicator 102 from the air. Thus, the indicator 102 is activated when the cap 104 is removed and the indicator 102 is exposed to the air. Once activated, information is then sent to the device 120 to indicate that the container 100 is open and the liquid 110 is ready to be consumed or dispensed. Thus, when the consumer ingests or drinks the liquid 110, the indicator 130 is activated and additional information is sent to the device 120. The correlation between the information from the indicator 102 and the indicator 130 determines if the consumer actually consumed the liquid 110 as well as the delay between opening the container 100 and consuming the liquid 110.

In accordance with another aspect of the present invention, the liquid 110 is non-conducting and thus the coating 130a is removed and only the unit 130b of the indicator 130 is included.

Figure 8:
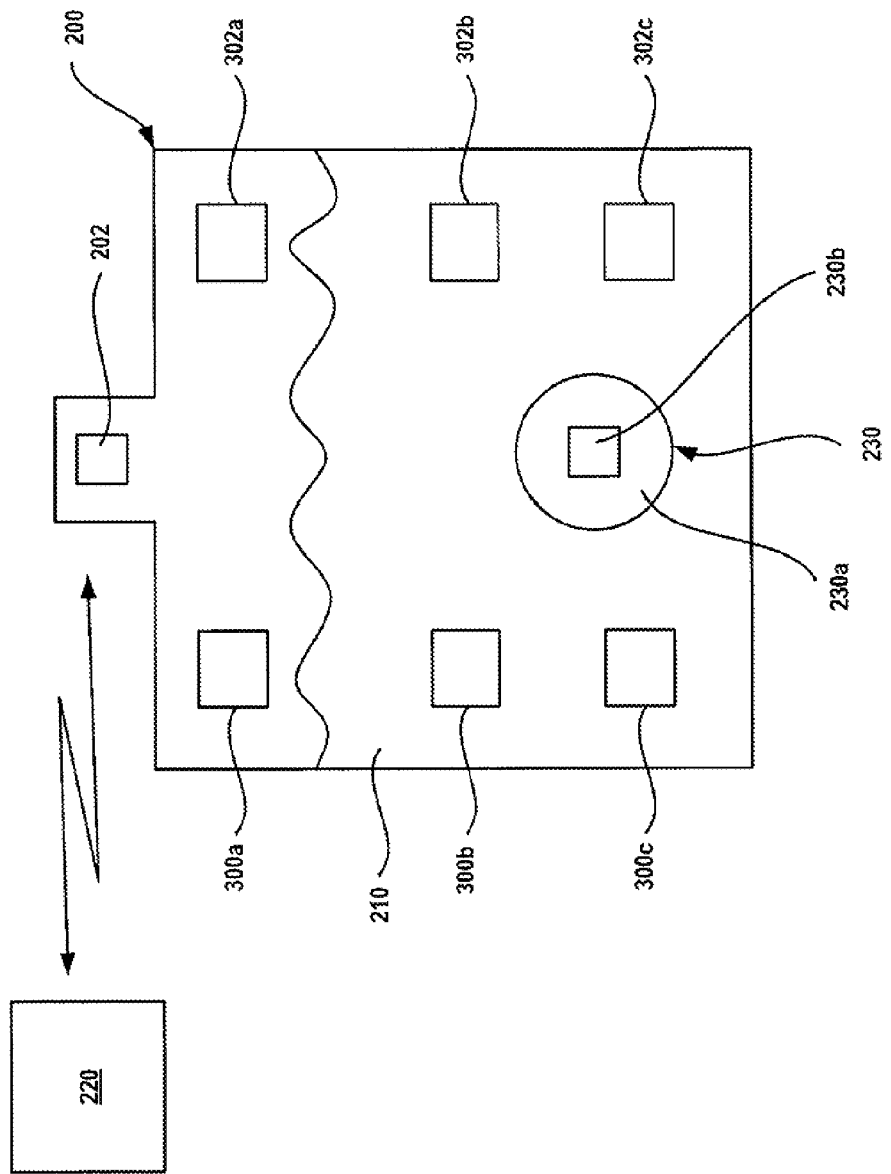
FIG. 8 shows a container for liquids with an event indicator and volume sensor in accordance with the teachings of the present invention.

Referring now to FIG. 8, a container 200 is shown similar to the container 100 that includes an event indicator 202 and an ingestible indicator 230. The container 200 holds liquid 210 that can be consumed. The scope of the present invention is not limited by the type of consumable liquid within container 200. The container 200 also includes sensors 300 (e.g. 300a-c) and 302 (e.g. 302a-c). In accordance with one aspect of the present invention, the sensors 300 and 302 include conductive ink that forms a capacitive plate pair. In accordance with another aspect of the present invention, the sensor 300 and 302 are made of traditional conduction material to form a capacitive pair. The sensor 300 forms one side of a capacitive coupler and the sensor 302 is the other side. For example the sensors 300a and 302a are one capacitive pair. The sensors 300 and 302 are secured to or positioned on the outside of the container 200. The sensor 300 and 302, in accordance with one aspect of the present invention, form a sensor for detection of change in content of the container 200. As the liquid 210 is removed, the capacitive characteristics between the sensors 300 and 302 changes. This change indicates the volume of liquid removed from the container 200. For example, the capacitance between the sensors 300a and 302a is different compared to the sensors 300b and 302b due to the type of material separating the sensors 300 and 302. In one instance it is air, in another it is the liquid 210, respectively. The sensors 300 and 302 can be positioned more or less proximal and the scope of the present invention is not limited by the relative distance separating the sensors 300 and 302. The more sensor pairs 300 and 302 that are included, the more accurate the measurement of the volume dispensed. This information can be communicated to a device 220.

In accordance with various aspects of the present invention, using the timing of activation of the indicator 202 and the activation of the indicator 230, as well as the information from sensor 300 and 302 information, the system can determine the volume of liquid consumed as well as the timing of the consumption of the content, such as the liquid 210, relative to the timing of opening the container 200 and the timing of dispensing the content of the container 200.

In accordance with another aspect of the present invention, as the consumer holds the container 200 and is wearing the device 220, then a transconduction signal is used to communicate information from the container 200 to the device 220. Furthermore, as indicated above, the sensor 200, based on the various aspects of the present invention, may be any of the sensor types, similar to sensor 100 of FIG. 7.

In accordance with the teachings of the present invention, there are various sources of information associated with the same container. For example: when a container is opened is one source of information; when a container is gripped or held by a consumer in one source of information; when the content of the container is dispensed is one source of information; when the container is in contact with the consumer's mouth is one source of information; when the content is ingested is one source of information; how much of the content is ingested is another source of the information; and the identity of the consumer is another source of information. Depending on the various aspects of the present invention, the information may be received by the device, such as the device 120 or device 220, wirelessly or through the consumer's body using transconduction.

In accordance with the present invention, if one consumer grips a container of the present invention, a signal is sent to device. The container includes sensors, such as sensors 300 and 302 of FIG. 8, that can be activated using a zinc-air battery or activated using a partial power source that is activated upon contact with moisture on the skin. This sensor can be protected from damage and activation by having a protective covering, such as a peel off label or similar covering. The next source of information is produced by having the lid or cap of the container is removed. Depending on the power source of the sensor located near the opening of the container, the information is either produced the moment the lid is removed or when the consumer's mouth comes into contact with the sensor located at the opening of the container. As the liquid is dispensed, the sensors, such as sensors 300 or 302, on the container detect changes in capacitance and pass that information to the device; the information can be sent through a wireless communication approach or through the user's body using transconduction by encoding the information in the current signature that the device detects. Another source of information is determining if the consumer ingested the content of the container and this is detected as a current signature from the ingestible sensors, such as sensors 130 or 230 that were ingested with the food.

Figure 9:
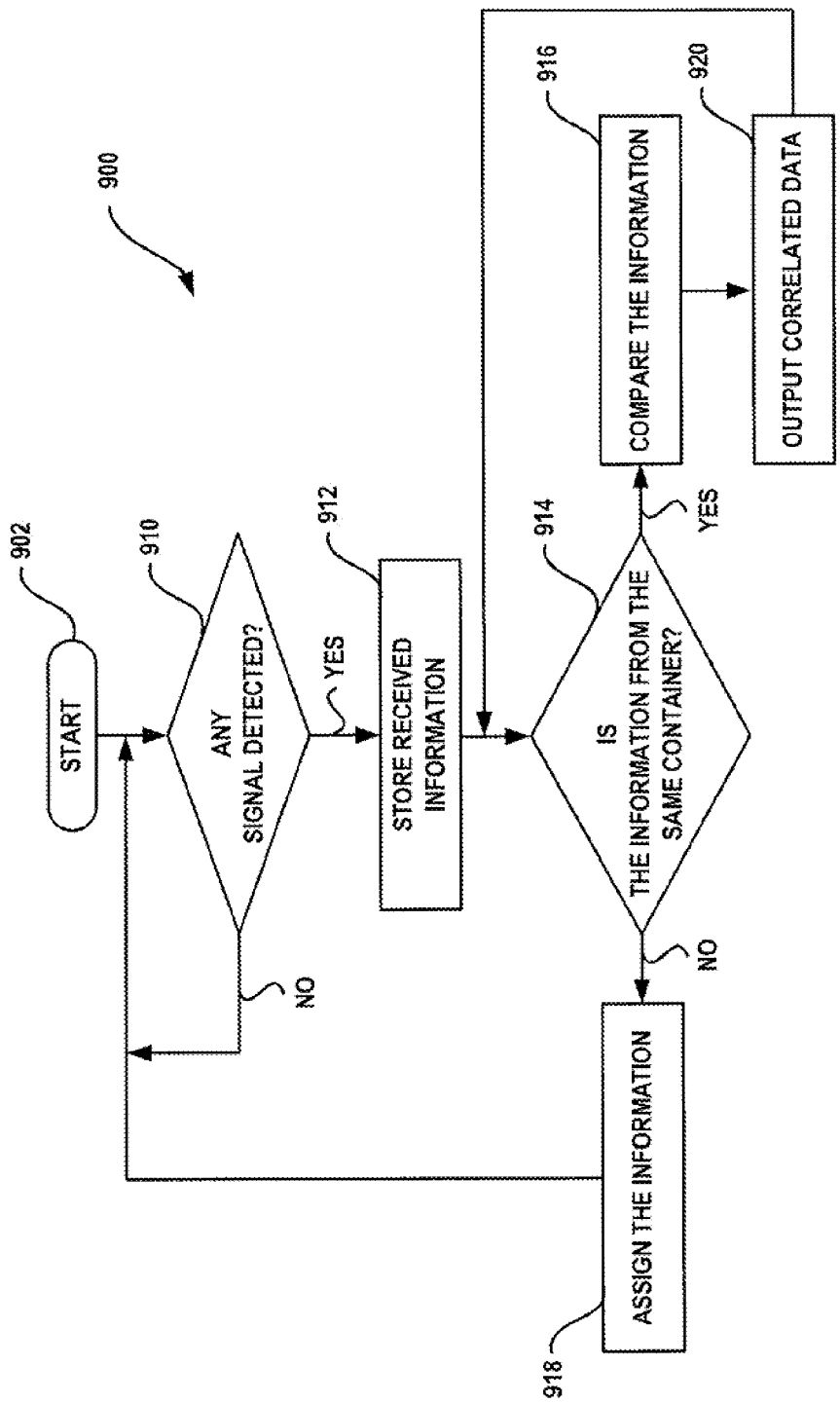
FIG. 9 is a process for collecting and correlating the information to automate tracking of food consumption by a consumer.

Referring now to FIG. 9, a flow process 900 is shown for collecting and correlating the information associated with the container, such as container 100 of FIG. 7 or container 200 of FIG. 8, to allow for automation of tracking food consumption by a consumer of the food. In accordance with the scope of the present invention, the information produces by the various sensors and indicators are uniquely associated with the container. Thus, if there were two containers sending information to the same device, the device can distinguish between the source of the information based on uniqueness of the information. The process 900 start at step 902. At step 910 a detector or receiver device, such as the device 120 or device 220, determines if there is any signal coming from an active indicator/sensor/capacitor pair, such as indicators 102, 202, 130, 230, 300 and 302. If there is information being send from any activate indicator/sensor/capacitor pair, then at step 912 the device stores the information including time and date associated with the information. Furthermore, the information may include identifying information about the product, which is also stored. If there is no active activate indicator/sensor/capacitor pair, then the process 900 waits at step 910. In accordance with one aspect of the present invention, the device may enter a sleep mode to conserver power is there is no active activate indicator/sensor/capacitor pair detected for a defined period of time. At step 914 the process 900 determines if the information collected is associated with the same container or a different container. If the information is associated with the same container, such as container 100, then at step 916 the device compares the time and date information with the other information recorded and outputs, at step 920, some correlated data about the container 100 or stored the correlated data. The process 900 then returns to step 914 to determine if there is new information or additional information about the same container to then correlated further. If the information is for a different container, then at step 918 the information is stored by the device until additional information is gathered from another active indicator/sensor/capacitor pair for the same container.

Identifiers of interest include two dissimilar electrochemical materials, which act similar to the electrodes (e.g., anode and cathode) of a power source. The reference to an electrode or anode or cathode are used here merely as illustrative examples. The scope of the present invention is not limited by the label used and includes the aspect wherein the voltage potential is created between two dissimilar materials. Thus, when reference is made to an electrode, anode, or cathode it is intended as a reference to a voltage potential created between two dissimilar materials.

When the materials are exposed and come into contact with the body fluid, such as stomach acid or other types of fluid (either alone or in combination with a dried conductive medium precursor), a potential difference, that is, a voltage, is generated between the electrodes as a result of the respective oxidation and reduction reactions incurred to the two electrode materials. A voltaic cell, or battery, can thereby be produced. Accordingly, in aspects of the invention, such power supplies are configured such that when the two dissimilar materials are exposed to the target site, e.g., the stomach, the digestive tract, etc., a voltage is generated.

In certain aspects, one or both of the metals may be doped with a non-metal, e.g., to enhance the voltage output of the battery. Non-metals that may be used as doping agents in certain aspects include, but are not limited to: sulfur, iodine and the like.

In accordance with the various aspects of the present invention, the system of the present invention can be inside specific food products (e.g. a granola bar), with one of the data encoded and communicated by the system being the caloric content of the food or other relevant dietary information e.g. fiber sugar content, fat type and content etc. This would help people on a diet monitor their daily intakes, get incentives for staying on-diet etc. Also, the system is co-ingested with food, using on-board sensing to measure food release into the stomach e.g. fat content. Also, an instrumented cup that detects when the system of the present invention has been dropped into the cup and whether the user or person took a drink (similar to inhaler product), and how much they drank. For example, the sensors 300 and 302 of FIG. 8 would indicated how much of the content of the container 200 was removed based on the change in capacitance between the various sensors 300 and 302 as explained above. An advantage of this aspect of the present invention is that it would automate the process of tracking food or regular supplements consumption.

In accordance with other aspects of the present invention, chemical markers can incorporate certain marker species into the food (e.g. salt, low-or-high pH, protein, and lipid). When ingested, a marker species is released into stomach environment. With the sensing capability, the system of the present invention can detect chemical-binding receptors on the surface or by coating on the system that reacts with a chemically-active coating (e.g. a coating such as a specific-ion-conducting glass membrane that allows only the desired marker species to penetrate). Co-ingest the system with the food, and use the system to measure/detect the presence of the "marker species". The system that is ingestible and masticable can contain a detector capable of measuring endocanabinoids. (see paper DiPatrizio et al, "Endocannabinoid signal in the gut controls dietary fat intake" for example reference, the entire disclose of which is incorporated herein by reference). When the signal is detected—a sign that high fat food intake has occurred—the user or patient is instructed via phone to take a prescription (also RIS-enabled) to disrupt the endocannabinoid signal, thus reducing the craving for more high fat foods.

In accordance with another aspect of the present invention, the system is detectable when the skirt is not present. In accordance with another aspect of the present invention, the ingestible sensors are safe to bite, for example by thinning the silicon. In accordance with another aspect of the present invention, several of the systems of the present invention are placed in the food so that if some get damaged during mastication the others are still functional. Thus, the systems could be distributed throughout the food, so that the number of systems detected gives an indication of the quantity of food consumed. Additionally, another aspect of the present invention teaches that the system of the present invention can be surrounded with gummy material and laminated between polymer layers that are soluble at low pH, but not in neutral pH (saliva). Furthermore, by reversing the coating, the opposite effect is achieved in accordance with another aspect of the present invention. First coat/laminate the system of the present invention with a pH sensitive polymer and then insert it inside gummy bites to help survive in the mouth. Thus, the system of the present invention is inside a gummy-bear like protective layer, and may be reduced in size, such as skirt-less or flexible skirt. The protective layer may consist of multilayers or may have a density or solubility gradient such that the material nearest the system is only slowly soluble and likely to be swallowed due to slippery surface, rounded shape and very small size. The system, according to another aspect of the present invention, would have a circuit modification that, in addition to probing the local impedance, has a feedback to postpone activation while the local impedance is high. This allows time for the remaining layer(s) to dissolve. The system is activated or turns on as soon as liquid penetrates through, but cannot send sufficient signal strength for detection, the high current and battery layer depletion is postponed until the impedance drops sufficiently. Thus, the system according to this aspect of the present invention, for example, is put into pre-measured meal and snack types to read out what was consumed.

It is to be understood that this invention is not limited to particular aspects or aspects described, as such may vary. It is also to be understood that the terminology used herein is for the purpose of describing particular aspects only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual aspects described and illustrated herein has discrete components and features which may be readily separated from or combined with the features of any of the other several aspects without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

What is claimed is:

1. A system for communication comprising:
   a container defining an opening and configured to contain a food, wherein the container includes a lid to secure the opening of the container and the food is an electrically conductive liquid; and
   an event indicator configured to transmit a signal, wherein the event indicator comprises:
      a support structure including a control module; and
      a partial power source comprising:
         a first material physically associated with the support structure; and
         a second material physically associated with the support structure at a location different from the location of the first material, such that the first material and second material are electrically isolated from each other and are configured to produce a voltage potential, wherein the control module is configured to control conductance between the first material and the second material when the partial power source is completed by the introduction of the electrically conductive liquid between the first material and the second material to complete the partial power source, and wherein the event indicator is secured to the container near the opening;

wherein the event indicator comprises a wireless transmitter configured to produce and transmit the signal when the lid is removed, the signal comprising information associated with a removal of the lid;

wherein at least one of the first material and second material is zinc, the voltage potential also being produced when the zinc reacts with air to produce the voltage potential to activate the event indicator as the lid is removed, wherein the event indicator produces and transmits the signal upon such activation; and an ingestible indicator located in the electrically conductive liquid and configured to transmit a second signal, wherein the ingestible indicator includes a coating to prevent interaction of the ingestible indicator with the electrically conductive liquid.

2. The system of claim 1, wherein the first material and the second material produce the voltage potential when in contact with the electrically conductive liquid as the electrically conductive liquid is dispensed through the opening of the container, the event indicator also being configured to be activated due to the first material and the second material coming in contact with the electrically conductive liquid.

3. The system of claim 2, wherein the event indicator produces a current signature that includes the information encoded therein using the control module.

4. The system of claim 2, wherein the ingestible indicator includes:
a second support structure;
a first dissimilar material physically associated with the second support structure of the ingestible indicator; and
a second dissimilar material physically associated with the second support structure of the ingestible indicator at a location different from the location of the first dissimilar material of the ingestible indicator, such that the first dissimilar material of the ingestible indicator indictor and second dissimilar material of the ingestible indicator are electrically isolated from each other and are configured to produce a second voltage potential,
wherein the second support structure of the ingestible indicator includes a second control module for controlling conductance between the first dissimilar material of the ingestible indicator and the second dissimilar material of the ingestible indicator.

5. The system of claim 4, wherein the ingestible indicator communicates with a detector associated with a consumer's body and wherein the detector receives and decodes the second signal comprising information produced by the ingestible indicator.

6. The system of claim 1, wherein the coating dissolves when in contact with a physiological fluid.

7. The system of claim 1, wherein the event indicator transmits the signal to a receiver secured to a consumer's skin.

8. The system of claim 1, further comprising a capacitive sensor secured to the container, wherein the capacitive sensor includes a pair of capacitive plates positioned on the container to allow for detection of the capacitance of the food of the container and wherein the capacitive sensor is configured to produce a third signal indicating at least one change in the capacitance of the container.

9. The system of claim 8, wherein the capacitive plates of the capacitive sensor comprise conductive ink.

10. A system for tracking food consumption by a consumer, the system comprising:
a container defining an opening and including a lid, wherein the container is configured to hold the food;
an ingestible indicator located in the food of the container and configured to communicate information, wherein the ingestible indicator comprises:
a support structure including a control module; and
a partial power source, comprising:
a first material physically associated with the support structure; and
a second material physically associated with the support structure at a location different from the location of the first material, such that the first material and second material are electrically isolated from each other and are configured to produce a voltage potential to activate the control module and to complete the partial power source by the introduction of a physiological fluid of a consumer between the first material and the second material, wherein the control module transmits the information to a receiver associated with the consumer upon being activated;
an event indicator secured near the opening of the container and protected by the lid, such that when the lid is removed, the event indicator is activated and transmits information associated with the lid being removed; and
a content sensor secured on a wall of the container to transmit a signal comprising information associated with a change in the container's food content, wherein the information from the event indicator and the information from the content sensor are transmitted to the receiver associated with the consumer.

11. The system of claim 10, wherein the event indicator transmits its information wirelessly and by using transconduction through the consumer's body and wherein the content sensor includes a unit to transmit its information using transconduction through the consumer's body.

12. The system of claim 11, wherein the event indicator and the content sensor are in communication such that activation of the event indicator results in a second signal being sent to the content sensor.

13. The system of claim 10, wherein the food is liquid and wherein a plurality of ingestible sensors are included in the liquid to produce information when the ingestible sensors are ingested, wherein the information is transmitted to the receiver using transconduction.

14. The system of claim 13 wherein the receiver includes a unit that is configured to correlate the information from the event indicator, the content sensor, and the ingestible sensors to automate the tracking of the food consumption by the consumer.

15. A method for automating the tracking of food consumption by a consumer, the method comprising the steps of:
activating an event indicator upon opening of a container that includes a food, wherein, upon activation, the event indicator transmits information to a receiver about the food's type and a time of the opening of the container and wherein the information from the event indicator is uniquely identifiable with the container;
activating, after the event indicator has been activated, a content sensor upon dispensing of the food, wherein the content sensor transmits information to the receiver about an amount of the food that is dispensed from the container wherein the information from the content sensor is uniquely identifiable with the container;

activating, after the content sensor has been activated, an ingestible indicator upon ingestion of the food by the consumer, wherein the ingestible indicator is ingestible and transmits information to the receiver to indicate the food has been consumed by the consumer wherein the information from the ingestible indicator is uniquely identifiable with the container; and correlating, at the receiver, at least two pieces of the information selected from the information group including information from the event indicator, the information from the content sensor, and the information from the ingestible indicator to automate tracking of the consumer's food consumption.

\* \* \* \* \*